US008171568B2

(12) United States Patent
Freitas et al.

(10) Patent No.: US 8,171,568 B2
(45) Date of Patent: May 1, 2012

(54) POSITIONAL DIAMONDOID MECHANOSYNTHESIS

(76) Inventors: Robert A. Freitas, Pilot Hill, CA (US); Ralph C. Merkle, Cupertino, CA (US)

(*) Notice: Subject to any disclaimer, the term of this patent is extended or adjusted under 35 U.S.C. 154(b) by 844 days.

(21) Appl. No.: 12/204,642

(22) Filed: Sep. 4, 2008

(65) Prior Publication Data

US 2009/0093659 A1    Apr. 9, 2009

Related U.S. Application Data

(60) Provisional application No. 60/970,658, filed on Sep. 7, 2007.

(51) Int. Cl.
  *G01Q 70/18* (2010.01)
  *G01Q 80/00* (2010.01)
  *B82B 3/00* (2006.01)
  *B82B 1/00* (2006.01)
(52) U.S. Cl. ............. 850/61; 850/62; 977/859; 977/877
(58) Field of Classification Search ............... 850/61, 850/62; 977/859, 877
See application file for complete search history.

(56) References Cited

U.S. PATENT DOCUMENTS

| | | | |
|---|---|---|---|
| 4,952,749 A | 8/1990 | Alexander et al. | |
| 4,987,312 A | 1/1991 | Eigler | |
| 5,144,148 A | 9/1992 | Eigler | |
| 5,372,659 A | 12/1994 | Lamaze et al. | |
| 5,824,470 A | 10/1998 | Baldeschwieler et al. | |
| 6,017,504 A | 1/2000 | Kaliaguine et al. | |
| 6,339,227 B1 | 1/2002 | Ellenbogen | |
| 6,348,700 B1 | 2/2002 | Ellenbogen et al. | |
| 6,422,077 B1 | 7/2002 | Krauss et al. | |
| 6,531,107 B1 | 3/2003 | Spencer et al. | |
| 6,716,409 B2 | 4/2004 | Hafner et al. | |
| 6,783,589 B2 | 8/2004 | Dahl | |
| 6,827,979 B2 | 12/2004 | Mirkin et al. | |
| 6,835,534 B2 | 12/2004 | Weiss et al. | |
| 6,864,481 B2 | 3/2005 | Kaito et al. | |
| 6,886,395 B2 | 5/2005 | Minne | |
| 6,987,277 B2 * | 1/2006 | Baur et al. ................. | 250/492.2 |
| 7,049,374 B2 | 5/2006 | Liu et al. | |
| 7,189,455 B2 | 3/2007 | Wong et al. | |

(Continued)

OTHER PUBLICATIONS

Robert A. Freitas Jr., "A Simple Tool for Positional Diamondiod Mechanosynthesis, and its Method of Manufacture". Unpublished United States patent application filed Feb. 11, 2005, claiming priority from U.S. Appl. No. 60/543,802, filed Feb. 11, 2004.

(Continued)

*Primary Examiner* — Jack Berman
(74) *Attorney, Agent, or Firm* — Terra Law LLP; Benedict O'Mahoney

(57) ABSTRACT

The invention provides methods of using positionally controlled molecular tools in an inert environment (such as ultra high vacuum) to fabricate complex atomically precise structures, including diamond, graphite, nanotubes, fullerenes, additional sets of the selfsame molecular tools, and others. Molecular tools have atomically precise tooltips which interact directly with a workpiece to add, remove, and modify specific atoms and groups of atoms, and have handles by which they can be held and positioned; tools can be recharged after use. Specific tooltips are brought into contact with and bond to specific feedstock molecules distributed on a presentation surface, and then transfer said feedstock molecules to specific atomic sites on a workpiece using mechanosynthetic chemical reactions. Specific sites on a workpiece can be made chemically reactive, facilitating the transfer of specific groups to them. Repeated applications of molecular tools at different locations on a workpiece can build a desired atomically precise structure.

35 Claims, 15 Drawing Sheets

U.S. PATENT DOCUMENTS

| | | |
|---|---|---|
| 7,211,795 B2 | 5/2007 | Collier et |
| 7,282,710 B1 | 10/2007 | Black et al. |
| 7,291,284 B2 | 11/2007 | Mirkin et al. |
| 7,309,476 B2 | 12/2007 | Carlson et al. |
| 7,326,293 B2 | 2/2008 | Randall et al. |
| 7,326,923 B2 | 2/2008 | Berstis |
| 7,381,625 B2 | 6/2008 | Xi et al. |
| 7,687,146 B1 | 3/2010 | Freitas, Jr. |
| 2009/0056802 A1 | 3/2009 | Rabani |

OTHER PUBLICATIONS

Jingping Peng, Robert A. Freitas Jr., Ralph C. Merkle, James R. Von Ehr, John N. Randall, George D. Skidmore, "Theoretical Analysis of Diamond Mechanosynthesis. Part III. Positional C2 Deposition of Diamond C(110) Surface using Si/Ge/Sn-based Dimer Placement Tools," J. Comput. Theor. Nanosci. 3 (Feb. 2006):28-41.

Berhane Temelso, C. David Sherrill, Ralph C. Merkle, Robert A. Freitas Jr., "High-level Ab Initio Studies of Hydrogen Abstraction from Prototype Hydrocarbon Systems," J. Phys. Chem. A 110 (Sep. 28, 2006):11160-11173.

Berhane Temelso, C. David Sherrill, Ralph C. Merkle, Robert A. Freitas Jr., "Ab Initio Thermochemistry of the Hydrogenation of Hydrocarbon Radicals Using Silicon, Germanium, Tin and Lead Substituted Methane and Isobutane," J. Phys. Chem. A 111(Aug. 15, 2007):8677-8688.

K. Eric Drexler, Nanosystems: Molecular Machinery, Manufacturing, and Computation, John Wiley & Sons, New York, 1992, Chapter 8.

D.M. Eigler, E.K. Schweizer, "Positioning Single Atoms with a Scanning Tunnelling Microscope," Nature 344(Apr. 5, 1990):524-526.

Noriaki Oyabu, Oscar Custance, Insook Yi, Yasuhiro Sugawara, Seizo Morita, "Mechanical vertical manipulation of selected single atoms by soft nanoindentation using near contact atomic force microscopy," Phys. Rev. Lett. 90(May 2, 2003):176102.

Ralph C. Merkle, "A proposed 'metabolism' for a hydrocarbon assembler," Nanotechnology 8(1997):149-162.

M.G. Hersam, G.C. Abeln, J.W. Lyding, "An approach for efficiently locating and electrically contacting nanostructures fabricated via UHV-STM lithography on Si(100)," Microelectronic Engineering 47(Jun. 1999):235-237.

D.H. Huang, Y. Yamamoto, "Physical mechanism of hydrogen deposition from a scanning tunneling microscopy tip," Appl. Phys. A 64(Apr. 1997):R419-R422.

J. Murota, M. Sakuraba, "Atomically controlled processing for high-performance Si-based devices," Tohoku-Cambridge Forum (Hall in Peterhouse, University of Cambridge, Organizers: M. Koyanagi, W.I. Milne), International Workshop on Nano-Technology, Nano-Materials, Nano-Devices, and Nano-Systems, Jun. 11, 2004.

J. Franks, "Preparation and properties of diamondlike carbon films," J. Vac. Sci. & Technol. A 7(May 1989):2307-2310.

C.A. Rego, P.W. May, E.C. Williamson, M.N.R. Ashfold, Q.S. Chia, K.N. Rosser, N.M. Everitt, "CVD diamond growth on germanium for infra-red window applications," Diam. Rel. Mater. 3(1994):939.

D.S. Patil, K. Ramachandran, N. Venkatramani, M. Pandey, R. d'Cunha, "Microwave plasma deposition of diamond-like carbon coatings," Pramana J. Phys. 55(Nov./Dec. 2000):933-939.

Y. Fukuda, M. Shimomura, G. Kaneda, N. Sanada, V.G. Zavodinsky, I.A. Kuyanov, E.N. Chukurov, "Scanning tunneling microscopy, high-resolution electron energy loss spectroscopy, and theoretical studies of trimethylphosphine (TMP) on a Si(111)-(7×7) surface," Surf. Sci. 442(1999):507-516.

M.J. Bronikowski, R.J. Hamers, "The chemistry of gallium deposition on Si(001) from trimethylgallium: an atomically resolved STM study," Surf. Sci. 348(Mar. 10, 1996):311-324.

D.M. Gruen, S. Liu, A. R. Krauss, X.Pan, "Buckyball microwave plasmas: Fragmentation and diamond-film growth," J. Appl. Phys. 75(1994):1758-1763.

Ansoon Kim, JaeYeol Maeng, Jun Young Lee, Sehun Kim, "Adsorption configuration and thermal chemistry of acetylene on the Ge(100) surface," J. Chem. Phys. 117(Dec. 8, 2002):10215-10222.

Guangquan Lu, John E. Crowell, "The adsorption and thermal decomposition of digermane on Ge(111)," J. Chem. Phys. 98(Feb. 15, 1993):3415-3421.

N. Oyabu, O. Custance, M. Abe, S. Moritabe, "Mechanical Vertical Manipulation of Single Atoms on the Ge(111)-c(2×8) Surface by Noncontact Atomic Force Microscopy," Abstracts of Seventh International Conference on Non-Contact Atomic Force Microscopy, Seattle, Washington, USA, Sep. 12-15, 2004.

P.D. Nellist, M.F. Chisholm, N. Dellby, O.L. Krivanek, M.F. Murfitt, Z.S. Szilagyi, A.R. Lupini, A. Borisevich, W.H. Sides, Jr., S.J. Pennycock, "Direct Sub-Angstrom Imaging of a Crystal Lattice," Science 305 (Sep. 17, 2004):1741.

G. Basile, P. Becker, A. Bergamin, G. Cavagnero, A. Franks, K. Jackson, U. Kuetgens, G. Mana, E.W. Palmer, C.J. Robbie, M. Stedman, J. Stumpel, A. Yacoot, G. Zosi, "Combined optical and X-ray interferometry for high-precision dimensional metrology", Proc. R. Soc. Lond. A (2000) 456, 701-729.

Y. Sugimoto, P. Pou, O. Custance, P. Jelinek, M. Abe, R. Perez, S. Morita, "Complex Patterning by Vertical Interchange Atom Manipulation Using Atomic Force Microscopy", Science 322, 413 (2008).

* cited by examiner

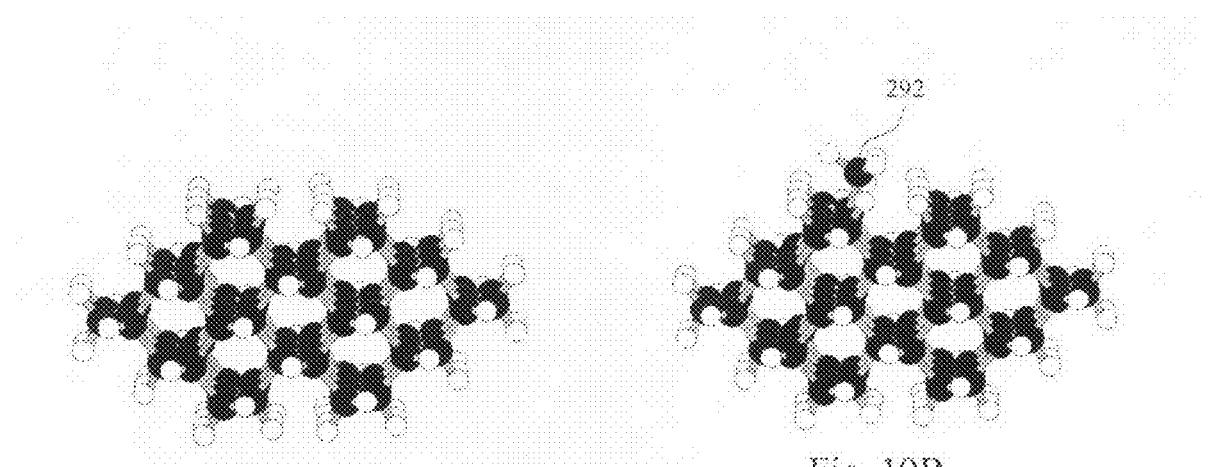
Fig. 19A
Fig. 19B
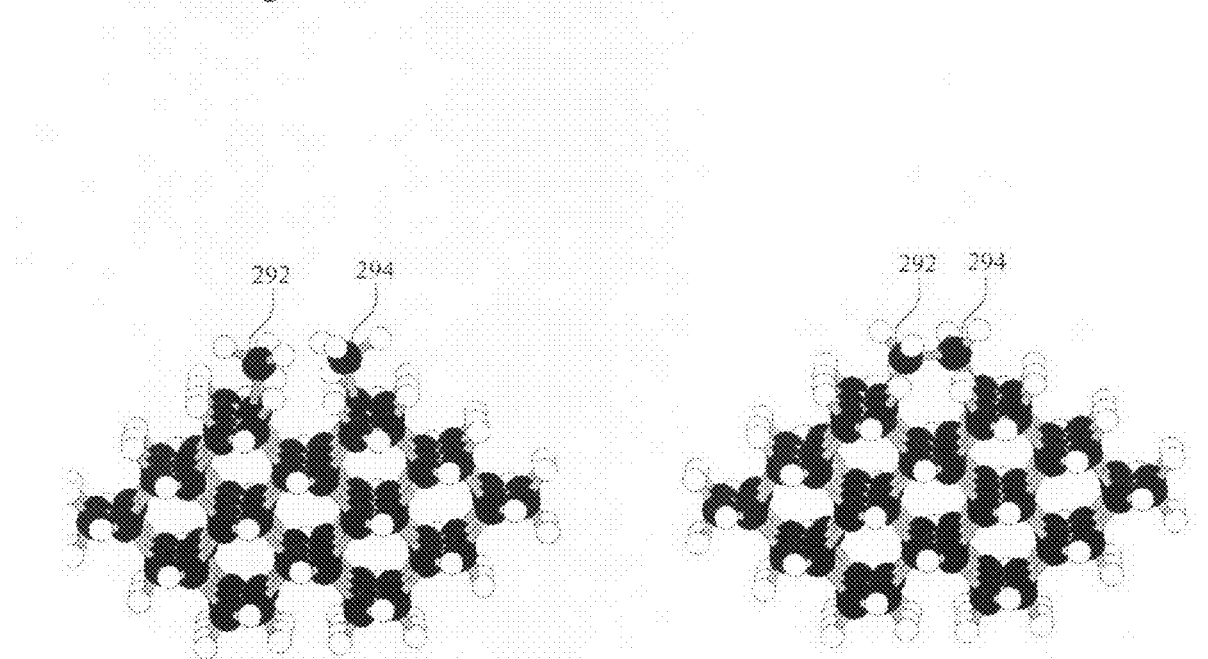
Fig. 19C
Fig. 19D

POSITIONAL DIAMONDOID MECHANOSYNTHESIS

CROSS-REFERENCE TO RELATION APPLICATIONS

This application claims the benefit of U.S. Provisional Patent Application No. 60/970,658 filed 7 Sep. 2007 by the present inventors.

FEDERALLY SPONSORED RESEARCH

Not applicable.

SEQUENCE LISTING OR PROGRAM

Not applicable.

TECHNICAL FIELD

The present application relates to mechanosynthesis, the fabrication of atomically precise tools and materials using individual atoms or small groups of atoms as the fundamental building blocks, and more particularly, to devices, methods and systems for performing ordered sequences of site-specific positionally controlled chemical reactions that are induced by use of mechanical force.

BACKGROUND

The present invention enables the molecular manufacturing of atomically precise diamond and diamondoid materials with fully deterministic atomic placement control. Diamondoid mechanosynthesis is the first known method to enable the fabrication of atomically precise diamond or diamondoid structures. No previously existing method for synthesizing diamond allows atomically precise diamond structures to be fabricated to atomic specifications with single-atom feature sizes.

Conventional Diamond Manufacturing. Conventional diamond manufacturing methods are bulk processes in which the diamond crystal structure is manufactured by statistical processes lacking positional control. In such processes, new atoms of carbon arrive at the growing diamond crystal structure having random positions, energies, and timing. Growth extends outward from initial nucleation centers having uncontrolled size, shape, orientation and location, yielding an inferior product having irregular atomic-scale features.

Existing bulk processes can be divided into three principal methods—(1) high pressure, (2) low pressure hydrogenic, and (3) low pressure nonhydrogenic.

(1) In the high pressure bulk method of producing diamond artificially, powders of graphite, diamond, or other carbon-containing substances are subjected to high temperature and high pressure to form crystalline diamond. High pressure processes are of several types:

(A) Impact Process. The starting powder is instantaneously brought under high pressure by applying impact generated by, for example, the explosion of explosives and the collision of a body accelerated to a high speed. This produces granular diamond by directly converting the starting powder material having a graphite structure into a powder composed of grains having a diamond structure. This process has the advantage that no press is required, as in the two other processes, but there is difficulty in controlling the size of the resulting diamond products. Nongraphite organic compounds can also be shock-compressed to produce diamond.

(B) Direct Conversion Process. The starting powder is held under a high static pressure of 13-16 GPa and a high temperature of 3,000-4,000° C. in a sealed high pressure vessel. This establishes stability conditions for diamond, so the powder material undergoes direct phase transition from graphite into diamond, through graphite decomposition and structural reorganization into diamond. In both direct conversion and flux processes, a press is widely used and enables single crystal diamonds to be grown as large as several millimeters in size.

(C) Flux Process. As in direct conversion, a static pressure and high temperature are applied to the starting material, but here fluxes such as Ni and Fe are added to allow the reaction to occur under lower pressure and temperature conditions, accelerating the atomic rearrangement which occurs during the conversion process. For example, high-purity graphite powder is heated to 1500-2000° C. under 4-6 GPa of pressure in the presence of iron catalyst, and under this extreme, but equilibrium, condition of pressure and temperature, graphite is converted to diamond: The flux becomes a saturated solution of solvated graphite, and because the pressure inside the high pressure vessel is maintained in the stability range for diamond, the solubility for graphite far exceeds that for diamond, leading to diamond precipitation and dissolution of graphite into the flux. Every year about 75 tons of diamond are produced industrially this way.

(2) In the low pressure hydrogenic bulk method of producing diamond artificially, widely known as CVD or Chemical Vapor Deposition, hydrogen ($H_2$) gas mixed with a few percent of methane ($CH_4$) is passed over a hot filament or through a microwave discharge, dissociating the methane molecule to form the methyl radical ($CH_3$) and dissociating the hydrogen molecule into atomic hydrogens (H). Acetylene ($C_2H_2$) can also be used in a similar manner as a carbon source in CVD. Diamond or diamond-like carbon films can be grown by CVD epitaxially on diamond nuclei, but such films invariably contain small contaminating amounts (0.1-1%) of hydrogen which gives rise to a variety of structural, electronic and chemical defects relative to pure bulk diamond. Hydrogen is generally regarded as an essential part of the reaction steps in forming diamond film during CVD, and atomic hydrogen must be present during low pressure diamond growth to: (1) stabilize the diamond surface, (2) reduce the size of the critical nucleus, (3) "dissolve" the carbon in the feedstock gas, (4) produce carbon solubility minimum, (5) generate condensable carbon radicals in the feedstock gas, (6) abstract hydrogen from hydrocarbons attached to the surface, (7) produce vacant surface sites, (8) etch (regasify) graphite, hence suppressing unwanted graphite formation, and (9) terminate carbon dangling bonds. Both diamond and graphite are etched by atomic hydrogen, but for diamond, the deposition rate exceeds the etch rate during CVD, leading to diamond (tetrahedral $sp^3$ bonding) growth and the suppression of graphite (planar $sp^2$ bonding) formation. (Most potential atomic hydrogen substitutes such as atomic halogens etch graphite at much higher rates than atomic hydrogen.) Currently, diamond synthesis from CVD is routinely achieved by more than 10 different methods. Low pressure or CVD hydrogenic metastable diamond growth processes are of several types:

(A) Hot Filament Chemical Vapor Deposition (HFCVD). Filament deposition involves the use of a dilute (0.1-2.5%) mixture of hydrocarbon gas (typically methane) and hydrogen gas ($H_2$) at 50-1000 torr which is introduced via a quartz tube located just above a hot tungsten filament or foil which is electrically heated to a temperature ranging from 1750-2800° C. The gas mixture dissociates at the filament surface, yielding dissociation products consisting mainly of radicals including $CH_3$, $CH_2$, $C_2H$, and CH, acetylene, and atomic hydrogen, as well as unreacted $CH_4$ and $H_2$. A heated deposition substrate placed just below the hot tungsten filament is held in a resistance heated boat (often molybdenum) and maintained at a temperature of 500-1100° C., whereupon diamonds are condensed onto the heated substrate. Filaments of W, Ta, and Mo have been used to produce diamond. The filament is typically placed within 1 cm of the substrate surface to minimize thermalization and radical recombination, but radiation heating can produce excessive substrate temperatures leading to nonuniformity and even graphitic deposits. Withdrawing the filament slightly and biasing it negatively to pass an electron current to the substrate assists in preventing excessive radiation heating.

(B) High Frequency Plasma-Assisted Chemical Vapor Deposition (PACVD). Plasma deposition involves the addition of a plasma discharge to the foregoing filament process. The plasma discharge increases the nucleation density and growth rate, and is believed to enhance diamond film formation as opposed to discrete diamond particles. There are three basic plasma systems in common use: a microwave plasma system, a radio frequency or RF (inductively or capacitively coupled) plasma system, and a direct current or DC plasma system. The RF and microwave plasma systems use relatively complex and expensive equipment which usually requires complex tuning or matching networks to electrically couple electrical energy to the generated plasma. The diamond growth rate offered by these two systems can be quite modest, on the order of ~1 micron/hour. Diamonds can also be grown in microwave discharges in a magnetic field, under conditions where electron cyclotron resonance is considerably modified by collisions. These "magneto-microwave" plasmas can have significantly higher densities and electron energies than isotropic plasmas and can be used to deposit diamond over large areas.

(C) Oxyacetylene Flame-Assisted Chemical Vapor Deposition. Flame deposition of diamond occurs via direct deposit from acetylene as a hydrocarbon-rich oxyacetylene flame. In this technique, conducted at atmospheric pressure, a specific part of the flame (in which both atomic hydrogen (H) and carbon dimers ($C_2$) are present) is played on a substrate on which diamond grows at rates as high as >100 microns/hour.

(3) In the low pressure nonhydrogenic bulk method of producing diamond artificially, a nonhydrogenic fullerene (e.g., $C_{60}$) vapor suspended in a noble gas stream or a vapor of mixed fullerenes (e.g., $C_{60}$, $C_{70}$) is passed into a microwave chamber, forming a plasma in the chamber and breaking down the fullerenes into smaller fragments including isolated carbon dimer radicals ($C_2$). (Often a small amount of $H_2$, e.g., ~1%, is added to the feedstock gas.) These fragments deposit onto a single-crystal silicon wafer substrate, forming a thickness of good-quality smooth nanocrystalline diamond (15 nm average grain size, range 10-30 nm crystallites) or ultrananocrystalline diamond (UNCD) diamond films with intergranular boundaries free from graphitic contamination, even when examined by high resolution TEM at atomic resolution. Fullerenes are allotropes of carbon, containing no hydrogen, so diamonds produced from fullerene precursors are hydrogen-defect free—indeed, the Ar/$C_{60}$ film is close in both smoothness and hardness to a cleaved single crystal diamond sample. The growth rate of diamond film is ~1.2 microns/hour, comparable to the deposition rate observed using 1% methane in hydrogen under similar system deposition conditions. Diamond films can, using this process, be grown at relatively low temperatures (<500° C.) as opposed to conventional diamond growth processes which require substrate temperatures of 800-1000° C.

Ab initio calculations indicate that $C_2$ insertion into carbon-hydrogen bonds is energetically favorable with small activation barriers, and that $C_2$ insertion into carbon-carbon bonds is also energetically favorable with low activation barriers. A mechanism for growth on the diamond C(100) (2×1):H reconstructed surface with $C_2$ has been proposed. A $C_2$ molecule impinges on the surface and inserts into a surface carbon-carbon dimer bond, after which the $C_2$ then inserts into an adjacent carbon-carbon bond to form a new surface carbon dimer. By the same process, a second $C_2$ molecule forms a new surface dimer on an adjacent row. Then a third $C_2$ molecule inserts into the trough between the two new surface dimers, so that the three $C_2$ molecules incorporated into the diamond surface form a new surface dimer row running perpendicular to the previous dimer row. This $C_2$ growth mechanism requires no hydrogen abstraction reactions from the surface and in principle should proceed in the absence of gas phase atomic hydrogen.

The UNCD films were grown on silicon (Si) substrates polished with 100 nm diamond grit particles to enhance nucleation. Deposition of UNCD on a sacrificial release layer of $SiO_2$ substrate is very difficult because the nucleation density is 6 orders of magnitude smaller on $SiO_2$ than on Si. However, the carbon dimer growth species in the UNCD process can insert directly into either the Si or $SiO_2$ surface, and the lack of atomic hydrogen in the UNCD fabrication process permits both a higher nucleation density and a higher renucleation rate than the conventional $H_2$/$CH_4$ plasma chemistry, so it is therefore possible to grow UNCD directly on $SiO_2$.

Besides fullerenes, it has been proposed that polymantanes, small hydrocarbons made of one or more fused cages of adamantane ($C_{10}H_{16}$, the smallest unit cage of hydrogen-terminated crystalline diamond) could be used as the carbon source in nonhydrogenic diamond CVD. It is suggested in U.S. Pat. No. 6,783,589 that the injection of polymantanes could facilitate growth of CVD-grown diamond film by allowing carbon atoms to be deposited at a rate of about 10-100 or more at a time, unlike conventional plasma CVD in which carbons are added to the growing film one atom at a time, possibly increasing diamond growth rates by an order of magnitude or better. Atomistic simulations to study thin-film growth via the deposition of very hot (119-204 eV/molecule; 13-17 km/sec) beams of adamantane molecules on hydrogen-terminated diamond C(111) surfaces, with forces on the atoms in the simulations calculated using a many-body reactive empirical potential for hydrocarbons, found that during the deposition process the adamantane molecules react with one another and the surface to form hydrocarbon thin films that are primarily polymeric with the amount of adhesion depending strongly on incident energy. Despite the fact that the carbon atoms in the adamantane molecules are fully $sp^3$ hybridized, the films contain primarily $sp^2$ hybridized carbon with the percentage of $sp^2$ hybridization increasing as the incident velocity goes up. However, cooler beams might allow more consistent $sp^3$ diamond deposition, and other techniques have deposited diamond-like carbon (DLC) films with a higher percentage of $sp^3$ hybridization from adamantane.

Positional Diamond Manufacturing via Mechanosynthesis. The positional assembly of diamondoid structures, some almost atom by atom, using molecular feedstock has been examined theoretically via computational models of diamondoid mechanosynthesis by Jingping Peng, Robert A. Freitas Jr., Ralph C. Merkle, James R. Von Ehr, John N. Randall, George D. Skidmore, "Theoretical Analysis of Diamond Mechanosynthesis. Part III. Positional $C_2$ Deposition on Diamond C(110) Surface using Si/Ge/Sn-based Dimer Placement Tools," J. Comput. Theor. Nanosci. 3(February 2006): 28-41; Berhane Temelso, C. David Sherrill, Ralph C. Merkle, Robert A. Freitas Jr., "High-level Ab Initio Studies of Hydrogen Abstraction from Prototype Hydrocarbon Systems," J. Phys. Chem. A 110 (28 Sep. 2006):11160-11173; Berhane Temelso, C. David Sherrill, Ralph C. Merkle, Robert A. Freitas Jr., "Ab Initio Thermochemistry of the Hydrogenation of Hydrocarbon Radicals Using Silicon, Germanium, Tin and Lead Substituted Methane and Isobutane," J. Phys. Chem. A 111(15 Aug. 2007):8677-8688; and K. Eric Drexler, Nanosystems: Molecular Machinery, Manufacturing, and Computation, John Wiley & Sons, New York, 1992, Chapter 8. Diamondoid mechanosynthesis is the controlled addition of individual carbon atoms, carbon dimers ($C_2$), single methyl ($CH_3$) or like groups to the growth surface of a diamond crystal lattice workpiece in a vacuum or other inert manufacturing environment. Covalent chemical bonds are formed one by one as the result of positionally constrained mechanical forces applied at the tip of a scanning probe microscope (SPM) apparatus.

The first experimental demonstration of positional atomic assembly of any kind occurred in 1989 when Eigler and Schweizer employed an SPM to spell out the IBM logo using 35 xenon atoms arranged on nickel surface, though no covalent bonds were formed. D. M. Eigler, E. K. Schweizer, "Positioning Single Atoms with a Scanning Tunnelling Microscope," Nature 344(5 Apr. 1990):524-526. The use of precisely applied mechanical forces to induce site-specific chemical transformations is called positional mechanosynthesis. In 2003, Oyabu et al achieved the first experimental demonstration of purely mechanical positional chemical synthesis (mechanosynthesis) on a heavy atom using only mechanical forces to make and break covalent bonds—first abstracting and then rebonding a single silicon atom to a silicon surface with SPM positional control in vacuum at low temperature using an atomically imprecise tip. Noriaki Oyabu, Oscar Custance, Insook Yi, Yasuhiro Sugawara, Seizo Morita, "Mechanical vertical manipulation of selected single atoms by soft nanoindentation using near contact atomic force microscopy," Phys. Rev. Lett. 90(2 May 2003):176102. In 2004, Oyabu et al repeated this experimental demonstration with a single Ge atom on a Ge surface. N. Oyabu, O. Custance, M. Abe, S. Moritabe, "Mechanical Vertical Manipulation of Single Atoms on the Ge(111)-c(2×8) Surface by Noncontact Atomic Force Microscopy," Abstracts of Seventh International Conference on non-contact Atomic Force Microscopy, Seattle, Wash., USA, 12-15 September 2004, p. 34.

The assumption of positionally controlled highly reactive tools operating in vacuum permits the use of novel and relatively simple reaction pathways. Following early general proposals in 1992 by Drexler for possible diamond mechanosynthetic tools and sketches of a few possible approaches to specific reaction pathways, in a partial set of tools and reaction pathways for diamondoid mechanosynthesis was outlined. Ralph C. Merkle, "A proposed 'metabolism' for a hydrocarbon assembler," Nanotechnology 8 (1997):149-162. Merkle's "hydrocarbon metabolism" scheme, which used 9 primary tooltypes plus several intermediates (some incompletely defined), employed at least 6 different element types (C, Si, Sn, H, Ne, and one unspecified transition metal), and required another unspecified "vitamin molecule" possibly including additional element types. It did not show 100% process closure, and in most cases did not specify complete reaction sequences.

The term "mechanosynthesis" is briefly mentioned in the text of U.S. Pat. No. 6,339,227 where it is undefined, and the related U.S. Pat. No. 6,348,700, where it is described as being facilitated by voltage pulses applied through an STM tip. Each of these references suffers from the disadvantage of not describing mechanically forcing a chemical reaction to occur.

Information relevant to attempts to address mechanically forcing a chemical reaction to occur can be found in U.S. Pat. Nos. 5,372,659 and 6,017,504. However, each one of these references suffers from the disadvantage of describing mechanically-forced chemical reactions that are not positionally controlled and not atomically precise.

Information relevant to attempts to address site-specific positional control of chemical reactions can be found in U.S. Pat. Nos. 4,987,312; 5,144,148; 6,987,277; and 7,326,923. However, each of these references suffers from the disadvantage that the described chemical reactions are driven by the application of voltages, electrical fields, electrostatic forces, or tunneling currents, and are not driven purely by the application of mechanical force.

Information relevant to attempts to address site-specific positional control of chemical reactions using mechanical force can be found in U.S. Pat. Nos. 5,824,470; 6,422,077; 6,716,409; 6,864,481; 6,886,395; and 7,189,455. However, each of these references suffers from the disadvantage that they employ atomically imprecise tips or employ bulk processes to prepare such tips.

Information relevant to attempts to address site-specific positional control of chemical reactions using mechanical force applied with atomically precise tips can be found in U.S. Pat. Nos. 6,827,979; 6,835,534; 7,211,795; 7,282,710; 7,291,284; 7,326,293; and 7,381,625. However, each of these references suffers from one or more of the following disadvantages: SPM tips are applied in nanolithographic processes that are not uniformly atomically precise; coatings or related bulk processes are employed; no chemical reactions are involved; or chemical reactions yield an atomically imprecise product.

Information relevant to attempts to address applications of extracting naturally occurring polyadmantane molecules, also referred to as diamondoids, from natural petroleum sources using bulk processes can be found in U.S. Pat. Nos. 4,952,749; 7,049,374; 7,309,476; and 7,312,562. However, each of these references suffers from the disadvantage that they do not teach that diamondoids can be manufactured using positionally controlled mechanosynthesis. Information relevant to attempts to address the use of molecular building blocks can be found in U.S. Pat. No. 6,531,107. However, this reference suffers from the disadvantages of specifying the use of large boron-based molecular building blocks, employing self-assembly rather than positional control, and yielding products that are not uniformly atomically precise.

Toolset for Diamondoid Mechanosynthesis. The minimal toolset includes nine specific tools, three of which have previously been discussed in the literature:

(A) Hydrogen Abstraction Tool. Undoped diamond normally consists of a rigid lattice of carbon atoms surface-passivated by hydrogen atoms, so a necessary aspect of diamond mechanosynthesis is the positionally-controlled abstraction (removal) of hydrogen atoms from stiff hydrocarbon structures—including hydrogens terminating the surface of the diamond crystal lattice, hydrogens present in feedstock molecules, and hydrogen atoms bonded to partly or fully completed mechanosynthetic tools or handle structures. The archetypal hydrogen abstraction tool described by Temelso et al. 2006 makes use of an ethynyl (acetylene) radical attached to a handle structure that first approaches a hydrogenated diamond surface as a site-specific active tool and then is retracted from a partially dehydrogenated diamond surface as a spent tool. The simplest practical HAbst tool is the ethynyl radical mounted on an adamantane base which is readily covalently bonded to a larger handle structure by extension of a regular diamond lattice of which the adamantane base is a unit cage. Site-specific hydrogen abstraction from crystal surfaces, though not purely mechanical abstraction, has also been achieved experimentally by abstracting an individual hydrogen atom from a specific atomic position in a covalently-bound hydrogen monolayer on a flat Si(100) surface, using an electrically-pulsed STM tip in ultrahigh vacuum. M. C. Hersam, G. C. Abeln, J. W. Lyding, "An approach for efficiently locating and electrically contacting nanostructures fabricated via UHV-STM lithography on Si(100)," Microelectronic Engineering 47(June 1999):235-237. However, this method suffers from the disadvantage that the described chemical reactions are driven by the application of voltages, electrical fields, electrostatic forces, or tunneling currents, and are not driven purely by the application of mechanical force.

(B) Hydrogen Donation Tool. Another necessary aspect of diamond mechanosynthesis is the positionally-controlled donation of hydrogen atoms to stiff hydrocarbon structures—including hydrogens terminating the surface of the diamond crystal lattice or to partly or fully completed mechanosynthetic tools or handle structures. The simplest hydrogen donation tool described by Temelso et al. 2007 is the Group IV-substituted adamantane such as the germanium-substituted adamantane that is brought up to a partially dehydrogenated diamond surface as a site-specific active tool and then is retracted from a now-rehydrogenated diamond surface as a spent tool. The Hydrogen Donation tool is readily covalently bonded to a larger handle structure by extension of a regular diamond lattice of which the adamantane base is a unit cage. Site-specific hydrogen donation to crystal surfaces, though not purely mechanical donation, has also been achieved experimentally by depositing hydrogen atoms from an STM tungsten tip to a monohydride Si(100)-H(2×1) surface by applying a +3.5V voltage bias to diffuse the hydrogens to the tungsten tip, followed by −8.5V 300 ms pulses to induce electronic excitations to break the W—H bond, in ultrahigh vacuum. D. H. Huang, Y. Yamamoto, "Physical mechanism of hydrogen deposition from a scanning tunneling microscopy tip," Appl. Phys. A 64(April 1997):R419-R422. However, this method suffers from the disadvantage that the described chemical reactions are driven by the application of voltages, electrical fields, electrostatic forces, or tunneling currents, and are not driven purely by the application of mechanical force.

(C) Dimer Placement Tool. A principal challenge in diamond mechanosynthesis is the controlled addition of carbon atoms to the growth surface of a diamond crystal lattice. One efficient method is to add a pair of triple-bonded carbon atoms (a $C_2$ dimer) in one operation. The function of a dimer placement tool described by Peng et al. is to position the dimer, then to bond the dimer at a precisely chosen lattice location on a growing molecular structure, and finally to withdraw the tool—leaving behind two carbon atoms bonded to the growing structure. This tool allows fabrication of diamond structures having an even number of C atoms that are geometrically accessible to the tool, given the limits imposed by tool aspect ratio. Monomer C and Ge atoms can more conveniently be transferred to diamondoid workpieces by adding .$CH_2$ groups using the Methylene or GermylMethylene tools, and by adding .$GeH_2$ groups using the Germylene tool.

Presentation Surfaces. Feedstock molecules are simple moieties consisting of one or a few atoms that are bonded to an atomically flat surface called the presentation surface. A tool can then be brought up under positional control to a specific atomic site on the presentation surface and bonded to the feedstock molecule, allowing the tool to remove the feedstock molecule from the presentation surface and then carry it away to participate in further mechanosynthetic operations, e.g., to add one or more atoms to a specific site on an atomically precise workpiece.

.$CH_2$ groups may be distributed on a germanium surface, facilitating their subsequent removal by a dehydrogenated silicon or diamond tool or tip, or on a silicon surface, by several means. For example, a partially methylated germanium surface is prepared by thermal adsorption and reaction of $CH_4$ gas on Ge(100) as described by J. Murota, M. Sakuraba, "Atomically controlled processing for high-performance Si-based devices," Tohoku-Cambridge Forum (Hall in Peterhouse, University of Cambridge, Organizers: M. Koyanagi, W. I. Milne), International Workshop on Nano-Technology, Nano-Materials, Nano-Devices, and Nano-Systems, 11 Jun. 2004; or by ion bombardment of clean Ge(111) at low substrate temperature (<470 K) using low-energy .$CH_3$ ions, a strongly exoergic radical coupling reaction. CVD of diamond and diamond-like carbon or DLC (C:H films) onto Ge substrates without carbide formation using $CH_4$ feedstock gas is well-known. J. Franks, "Preparation and properties of diamondlike carbon films," J. Vac. Sci. & Technol. A 7(May 1989):2307-2310; and C. A. Rego, P. W. May, E. C. Williamson, M. N. R. Ashfold, Q. S. Chia, K. N. Rosser, N. M. Everitt, "CVD diamond growth on germanium for infra-red window applications," Diam. Rel. Mater. 3 (1994):939. (Absorption spectra after hydrocarbon CVD on Ge surfaces indicate that bonding is mainly type $sp^3$ with CH, $CH_2$, and $CH_3$ bonds [O]; a similar experiment on Si substrate found 19.4% $sp^3$ $CH_3$, 23.4% $sp^3$ $CH_2$, and 45.6% $sp^3$ CH species by observing C—H stretch absorption bands. D. S. Patil, K. Ramachandran, N. Venkatramani, M. Pandey, R. d'Cunha, "Microwave plasma deposition of diamond-like carbon coatings," Pramana J. Phys. 55(November/December 2000):933-939.) Related techniques such as physical vapor deposition (PVD), laser CVD, direct ion beam deposition, dual ion beam sputtering, RF/DC glow discharge or microwave discharge may also be employed. The dissociation of trimethylphosphine (see Y. Fukuda, M. Shimomura, G. Kaneda, N. Sanada, V. G. Zavodinsky, I. A. Kuyanov, E. N. Chukurov, "Scanning tunneling microscopy, high-resolution electron energy loss spectroscopy, and theoretical studies of trimethylphosphine (TMP) on a Si(111)-(7×7) surface," Surf. Sci. 442 (1999): 507-516) on Si(111) and trimethylgallium (see M. J. Bronikowski, R. J. Hamers, "Adsorption and Dissociation of Trimethylgallium on Si(001): An Atomically Resolved STM Study," Surf. Sci. 348(10 Mar. 1996):311-324) on Si(100) via thermal annealing at 400-500 K leaves isolated .$CH_2$ groups on these surfaces. A $CH_3$-decorated Ge surface may also be prepared via conventional solution-phase chemical methylation since methylated germanium is found in the natural environment; each $CH_3$ is converted to .$CH_2$ using a proto-HAbst or an HAbst tool. $C_2$ (see D. M. Gruen, S. Liu, A. R. Krauss, X. Pan, "Buckyball microwave plasmas: Fragmentation and diamond-film growth," J. Appl. Phys. 75 (1994):1758-1763), $C_2H_2$ (see Ansoon Kim, Jae Yeol Maeng, Jun Young Lee, Sehun Kim, "Adsorption configuration and thermal chemistry of acetylene on the Ge(100) surface," J. Chem. Phys. 117(8 Dec. 2002):10215-10222), and .$GeH_2$ (see Guangquan Lu, John E. Crowell, "The adsorption and thermal decomposition of digermane on Ge(111)," J. Chem. Phys. 98(15 Feb.

1993):3415-3421) groups can also be distributed on flat silicon or germanium surfaces, providing a convenient presentation surface for carbon dimer and germanium feedstock molecules.

Bootstrapping. Once the first atomically precise tools exist, they can be used to fabricate more of the self-same tools. But the first set of atomically precise tools must be manufactured using only currently available atomically imprecise tools, or proto-tools, a process called bootstrapping. Numerous approaches exist for bootstrapping the first tools from proto-tools, but several examples can be given here. One approach is to synthesize appropriate molecules and then attach these (or similar molecules that have appropriate tooltip structure) to the tip structure of an SPM-like device to create the first proto-tools via tip functionalization; a wide range of molecular structures having the desired functionality similar to atomically precise tools are feasible. Another approach using commercially available SPM ultrasharp tips is disclosed in the detailed description below. Commercially available tips have been used to scan short poly(dG)-poly(dC) DNA fragments deposited on modified HOPG (highly oriented pyrolytic graphite), enabling detection of single-stranded regions in double-stranded poly(dG)-poly(dC) and double-stranded and single-stranded regions in poly(dG)-poly(dG)-poly(dC) triplexes, as well as the resolution of the helical pitch of the triplex molecules. SPM instruments can already achieve the requisite sub-Angstrom positioning accuracy needed for reliable site-specific atomically precise mechanosynthesis operations.

SUMMARY

The present invention is directed to an apparatus and method that satisfies the need for performing positional diamondoid mechanosynthesis.

Apparatuses according to the present embodiments include a tooltip that includes a first group of atoms that actively participate in a chemical reaction and a second group of atoms that hold the first group in the correct position to enable the reaction to occur. In another embodiment, a tooltip and a workpiece, both under continuous positional control, are brought together to force a single site-specific chemical reaction to occur; the tooltip may also form a new bond to the workpiece, and one or more atoms may be transferred between the tooltip and the workpiece.

In another embodiment, an already-bonded tooltip and a workpiece, both under continuous positional control, do not detach when further tooltip motion causes a change in workpiece. In another embodiment, a tooltip whose "second group of atoms" consists of a polycyclic molecular structure is composed of one or more of the elements C, N, O, and H (or replacement elements having the same valences) with at least one of these elements in a bridgehead or sidewall position. Additionally, a tooltip structural atom could consist of a bridgehead or sidewall atom where that atom is chosen from a specific list of chemical elements; a tooltip structural atom could have none or one single-atom transfer payload where the single atom is chosen from a specific list of chemical elements; a tooltip structural atom could have a transfer payload consisting of two, three, or four atoms, each chosen from a specific list of chemical elements; a tooltip structural atom could be bonded to one C atom of a C2 dimer, and the other C atom of the C2 dimer could be bonded to none or a single atom chosen from a specific list of chemical elements; a multiple number of tooltips could be operated in parallel to perform a multiple number of reactions; and a multiple number of tooltips could be operated together to perform a single reaction.

In another embodiment, a tool is comprised of a tooltip attached to a passive handle that can be manipulated by a system capable of atomically precise positional control. Additionally, the molecular structure of a tool handle can be chosen from a specific list of adamantane- and diamond-related structures; a tool can be reversibly bonded to a workpiece so that manipulating the handle permits manipulating the workpiece without adding or removing any atoms from the workpiece; multiple tooltips can be affixed on one handle to form a multi-tooltip tool; and a multiple number of tooltips can be operated together to perform a single reaction.

In another embodiment, a tooltip or tool is attached to a positioning device that can exert atomically precise positional control. Additionally, the tooltip can be forced to follow a specified trajectory relative to the workpiece, causing a site-specific reaction to occur on the workpiece; a tooltip can be bonded to a workpiece so that manipulating the handle causes a change in workpiece structure or electronic state without detaching the tooltip from the workpiece.

Methods according to the present embodiments include guiding a tooltip to a workpiece, whereupon the application of positionally controlled mechanical force causes a mechanosynthetic chemical reaction to occur between tooltip and workpiece. Additionally, a chemical bond could be formed between tooltip and workpiece; one or more atoms could be transferred between tooltip and workpiece; completion of one or more reactions could put the system into one well-defined state; completion of one or more reactions probabilistically could put the system into one well-defined state, of several possible such states; one or more reaction steps or sequences could be used to fabricate a mechanosynthetic tooltip or tool, whether in charged or discharged condition; one or more reaction steps or sequences could be used to recharge a mechanosynthetic tooltip or tool that has become discharged during use; one or more reaction steps or sequences could be used to fabricate atomically precise diamondoid structures of any size or permissible crystalline geometry; one tooltip already attached to a workpiece could be exchanged for another tooltip also attached to the workpiece without adding or removing any atoms from the workpiece; one tooltip already attached to a workpiece could be exchanged for another tooltip also attached to the workpiece while adding or removing one or more atoms from the workpiece; a tooltip having a $CH_n$ (n=0-3) payload could be mechanosynthetically bonded to an atomically precise workpiece type selected from a specific list of such types; one or more ring structures or cages of an adamantane-like structure could be fabricated using combinations of ring-closing reaction sequences selected from a specific list of such sequences; a diamond C(110) surface could be extended by a chain deposition process using a one-handled polyene chain that is applied in a zigzag pattern across a C(110) trough to build the next layer; two handles bonded to an intermediate workpiece could be pulled apart to create two separate mechanosynthetic tools, with each tool in one of two possible known well-defined states that can be determined by testing; two handles bonded to an intermediate workpiece could be pulled apart to create two separate mechanosynthetic tools, with each tool in one of two possible known well-defined states that can be used without testing; a hydrogen donation tool could be presented in turn to two sites, either of which may have a radical, thus definitely ensuring that whichever site has the radical becomes hydrogenated; positionally controlled bond angle bending could be employed during a mechanosynthetic reaction to improve reaction reliability; force could be applied along different vectors by one or more mechanosynthetic tools to precisely control the site of bond breakage; and one or more reactions could be omitted from a reaction sequence because they are not needed to complete a previous or following reaction sequence in a series of two or more reaction sequences.

In another embodiment, a tooltip, already bonded to a workpiece, is moved under continuous positional control, causing a change in workpiece state without detaching the tooltip. In another embodiment, a Dimer Placement Tool is recharged by bonding the tooltip of the discharged tool to an acetylene molecule from a hot gas, then abstracting the two hydrogen atoms from the bonded acetylene molecule.

In another embodiment, feedstock molecules are provided for mechanosynthetic chemical reactions on a presentation surface. In another embodiment, a mechanosynthetic tool is built using only atomically imprecise positionally controlled tips.

Materials according to the present embodiments include materials produced by using positionally-controlled mechanosynthetic chemical reactions. Additionally, the material could have the same structure as a mechanosynthetic tooltip or tool, whether in charged or discharged condition; one or more reaction steps or sequences could be used to fabricate atomically precise diamondoid structures of any size or permissible crystalline geometry; and one or more reaction steps or sequences could be used to fabricate atomically precise structures of any size or permissible crystalline geometry.

Systems according to the present embodiments include a system of tooltips, tools, reactions, and reaction sequences that can fabricate all of the self-same tooltips and tools and can execute all of the self-same reactions and reaction sequences. Additionally, the set of tools could be used to make all of the tools in the same toolset; and the set of methods could be used to perform all of the processes required for diamondoid mechanosynthesis. Another embodiment describes a system of tools and reactions that can make multi-atom 3D structures using mechanosynthesis.

Arranging atoms in most of the ways permitted by physical law is a fundamental objective of molecular manufacturing. An advantage of the present invention is the ability to synthesize atomically precise diamondoid structures using positionally controlled molecular tools.

Another advantage the present invention provides is that using only simple bulk-produced inputs, a 9-tooltype minimal toolset can be created that can: (1) fabricate all nine tooltypes, including their adamantane handle structures and reactive tool intermediates, starting from flat passivated diamond surface or a handle-bound adamantane seed structure; (2) recharge all nine tooltypes after use; and (3) build both clean and hydrogenated molecularly-precise unstrained cubic diamond C(111)/C(110)/C(100) and hexagonal diamond (lonsdaleite) surfaces of process-unlimited size including some Ge-substituted variants, methylated and ethylated surface structures, and also handled polyene, polyacetylene and polyethylene chains of process-unlimited length, along with both flat graphene sheet and curved graphene nanotubes.

Another advantage of the present invention is that 100% process closure can be achieved using a minimal toolset for diamond mechanosynthesis consisting of only three primary tooltypes assisted by six auxiliary structures.

These and other features, aspects, and advantages of the present invention will become better understood with reference to the following description and claims.

BRIEF DESCRIPTION OF THE DRAWINGS

For a more complete understanding of the present invention, reference is now made to the following descriptions taken in conjunction with the accompanying drawings, in which:

FIG. 19A shows a small section of diamond C(110) surface representing an atomically precise workpiece upon which the C(110) surface is exposed;

FIG. 19B shows a diamond C(110) atomically precise workpiece surface with a $CH_3$ group bonded to a specific atom on the left side of a trough;

FIG. 19C shows a diamond C(110) atomically precise workpiece surface with a $CH_3$ group bonded to a specific atom on the left side of a trough and a second methyl group bonded to a specific neighboring atom on the right side of the same trough; and FIG. 19D shows two $CH_2$ groups bonded across a trough on a diamond C(110) atomically precise workpiece surface.

DETAILED DESCRIPTION

Figure 1A:
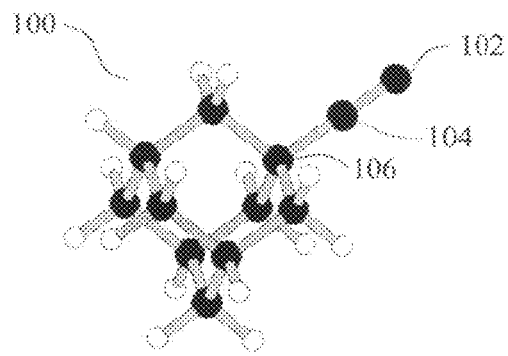
FIG. 1A is an active Hydrogen Abstraction Tool.

The following definitions are used herein to more particularly describe the present invention.

An "adamantane" molecule comprises a 3D cage structure of ten carbon atoms, each terminated with one or two hydrogen atoms, having the chemical formula $C_{10}H_{16}$ and representing the smallest possible unit cage of crystalline diamond.

An "adamantane molecular structure" is a molecular structure that is similar to and may include a single adamantane molecule, but also includes adamantane molecules which (1) may lack one or more terminating atoms, (2) may be covalently bonded to one or more neighboring adamantane cages in various well-known crystallographic lattice geometries, and (3) may employ elements other than carbon and hydrogen to form equivalent cage or crystallographic lattice geometries.

An "adamantane-like molecular structure" is (1) any polycyclic closed shell molecular structure composed entirely of carbon, nitrogen, oxygen and hydrogen, or (2) any molecular structure as in (1) that has been modified by substituting one or more atoms which, in the substituted molecular structure, have similar valence to the substituted carbon, nitrogen, oxygen or hydrogen atoms. By way of example, and not of limitation, an adamantane-like molecular structure would include adamantane, polymantanes, heteroadamantanes, iceane, cubane, pagodane, dodecahedrane, cage or polycyclic hydrocarbons, graphene, fullerenes, carbon nanotubes, diamond shards terminated by hydrogen, fragments of lonsdaleite terminated with hydrogen, fragments of silicon or germanium terminated by hydrogen, fluorine terminated adamantane, or incompletely terminated polymantanes.

The "bridgehead position" of an adamantane-like molecular structure refers to a structural atom that is bonded to three other structural atoms and is terminated by one or more non-structural atoms.

A "chemical bond" is an interatomic covalent bond or an interatomic ionic bond, as these terms are commonly understood by practitioners skilled in the art.

A "chemical reaction" is said to occur when chemical bonds are formed or broken, or when the directionality, strength, or other salient characteristics of an existing chemical bond is altered by mechanical means, as for example during positionally controlled bond bending.

A "chemical reaction driven by the application of mechanical force" refers to a chemical reaction that is (1) driven through its reaction barrier by mechanically forcing reactants or products through the transition state, (2) potentially reactive sites are driven away from a competing undesired reaction by mechanically restraining potentially reactive sites from attaining closer physical proximity, or (3) allowed to occur by bringing potentially reactive sites into closer physical proximity when zero mechanical force is required to do so, as for example when no reaction barrier exists. The use of tunneling currents flowing directly between potentially reactive sites, or the employment of bias voltages, ramp voltages, voltage pulses, or electric fields to elicit the formation of electric dipoles or tunneling currents flowing directly between potentially reactive sites, solely for the purposes of inducing a chemical reaction between those potentially reactive sites or inducing field evaporation of passivating atoms is excluded from "mechanosynthesis". Similarly, the use of mechanical force to push molecules across a surface where no chemical reactions are induced is excluded from "mechanosynthesis".

"Diamond" is a hydrocarbon adamantane molecular structure consisting of repeating adamantane cage units arranged in various well-known crystallographic lattice geometries.

"Diamondoid" materials include any stiff covalent solid that is similar to diamond in strength, chemical inertness, or other important material properties, and possesses a dense three-dimensional network of bonds. Examples of such materials include but are not limited to (1) diamond, including cubic and hexagonal lattices and all primary and vicinal crystallographic surfaces thereof, (2) carbon nanotubes, fullerenes, and other graphene structures, (3) several strong covalent ceramics of which silicon carbide, silicon nitride, and boron nitride are representative, (4) a few very stiff ionic ceramics of which sapphire (monocrystalline aluminum oxide) is representative, and (5) partially substituted variants of the above that are well-known to those skilled in the art.

A "handle structure" comprises a plurality of atoms whose bonding pattern or electronic state is not altered during a site-specific mechanosynthetic chemical reaction and whose primary function is to hold a mechanosynthetically active tooltip or tool in a fixed geometric relationship that will permit a mechanosynthetic chemical reaction to proceed when the handle is manipulated by a positional device. Handle structure may include the null case.

An "inert environment" includes, but is not limited to, UHV, helium, neon, or other noble gases either individually or in combination, or other gases or liquids that do not react with the tooltip or workpiece during mechanosynthetic operations.

"Mechanical force" may include applied mechanical forces having positive, negative, or zero magnitude, but excludes the application of electrical voltages or the utilization of electrical current flows to induce a site-specific chemical reaction to occur.

"Mechanosynthesis" is the making or breaking of chemical bonds by the application of site-specific positionally-controlled mechanical force, allowing the fabrication of multi-atom structures.

A "mechanosynthetically active tooltip" is a tooltip controlled by a positional device that can perform mechanosynthetic reactions.

A "mechanosynthetic reaction" (sometimes referred to as a "reaction" when context makes it clear that the reaction is mechanosynthetic) is an individual chemical reaction that is driven to completion by the application of mechanical force.

A "mechanosynthetic reaction sequence" (sometimes referred to as a "reaction sequence" when context makes it clear that the reaction sequence is mechanosynthetic) is a series of individual reactions arranged in an ordered sequence that permits the fabrication of complex atomically precise structures comprising a plurality of atoms and chemical bonds.

A "positional device" is a device capable of exerting atomically precise positional control on a mechanosynthetic tooltip, tool, or workpiece, and may include, but is not limited to, a conventional scanning probe microscope (SPM) such as an atomic force microscope (AFM), a miniaturized or MEMS-scale SPM or AFM, a robotic arm mechanism of any size scale, or other appropriate manipulation system capable of atomically precise positional control.

The "sidewall position" of an adamantane-like molecular structure refers to a structural atom that is bonded to two other structural atoms and is terminated by one or more nonstructural atoms.

A "structural atom" in an adamantane-like molecular structure refers to an atom comprising the cage framework, for example a carbon atom in an adamantane molecule.

A "structural substituent atom" is an atom that occupies either a bridgehead or a sidewall position in an adamantane-like molecular structure.

A "terminating atom" in an adamantane-like molecular structure refers to an atom that does not serve as a constituent atom in the cage structure but absorbs unused valences of a structural atom comprising the cage framework, for example a hydrogen atom in an adamantane molecule.

A "tool" is an atomically precise mechanosynthetically active tooltip covalently bonded to a handle structure.

A "toolset" is a selected set of mechanosynthetic tools.

A "tooltip" is an atomically precise device comprising a first atom or plurality of atoms whose bonding pattern or electronic state is capable of being altered when brought into mechanical contact with other tooltips or with a workpiece during a site-specific mechanosynthetic chemical reaction, and a second atom or plurality of atoms whose bonding pattern or electronic state is not altered during a site-specific mechanosynthetic chemical reaction and whose primary function is to hold the first plurality of atoms in a fixed geometric relationship that will permit a mechanosynthetic chemical reaction to proceed.

A "transfer passivating atom" is an atom that passivates one or more open valences of a transfer substituent atom.

A "transfer substituent atom" is an atom that terminates a structural substituent atom via a single covalent bond, and that may be chemically transferred to a workpiece during a site-specific positionally-controlled mechanosynthetic chemical reaction driven by the application of mechanical force.

The present invention proposes a realizable pathway for the creation of a set of mechanosynthetic molecular tools that are able to fabricate the self-same set, or refresh all tools in the set, or build a wide range of product structures. We describe a set of mechanosynthetic tools that achieves all these objectives, and then describe a bootstrap process to build the first set of such tools.

While a few of these mechanosynthetic tools have been discussed in the theoretical literature, none of them have been experimentally realized nor has a set of tools been proposed with the above described properties.

The set of mechanosynthetic molecular tools comprises: (1) the Hydrogen Abstraction Tool, shown in FIG. 1; (2) the Hydrogen Donation Tool, shown in FIG. 2; (3) the Germanium Radical Tool, shown in FIG. 3; (4) the Methylene Tool, shown in FIG. 4; (5) the GermylMethylene Tool, shown in FIG. 5; (6) the Germylene Tool, shown in FIG. 6; (7) the Hydrogen Transfer Tool, shown in FIG. 7; (8) the Adamantane Radical Tool, shown in FIG. 8; and (9) the Dimer Placement Tool, shown in FIG. 9.

While this specific set of tools has the desired properties, e.g., the ability to fabricate and refresh all the tools in the toolset as well as the ability to make a wide range of other products (in this case, a wide range of structures composed of hydrogen, carbon and germanium) it is given as a specific example and it should be understood that other sets of mechanosynthetic tools would readily come to mind to one skilled in the art and having the benefit of the teachings presented herein. Besides the mechanosynthetic tools, we also describe the mechanosynthetic reactions which those tools enable.

In the following description, we describe how, given a sufficient number of each type of molecular tool, we can fabricate more molecular tools of any given type, how to recharge the molecular tools, and how to use the molecular tools to fabricate other molecular structures.

The invention is used to fabricate atomically precise multi-atom structures. The particular toolset illustrated here is used to build atomically precise structures from hydrogen, carbon and germanium. The ideas and concepts readily extend to a wider range of elements and structures.

The present invention has many advantages, including the ability to fabricate complex structures to atomically precise specifications, the ability to position individual atoms or groups of atoms in specific locations on a workpiece, the ability to remove specific groups of atoms from specific sites on a workpiece, the ability to make atomically precise modifications to a workpiece, the ability to make specific sites on a workpiece become reactive while the rest of the workpiece remains relatively unreactive, and the ability to make specific sites on a workpiece become unreactive.

The nine principal tools have been listed above. A detailed description of these tools follows. For clarity, all Figures show only the active tooltips and a few supporting atoms but do not show the handle structure that is attached to each tooltip to make the complete tool, since the handle structure can be much larger than the tooltip and the site of mechanosynthetic chemical activity is the tooltip, not the handle. The handle structure provides the means by which the molecular tools can be held and moved with translational and rotational precision.

(1) The Hydrogen Abstraction Tool. FIG. 1A illustrates the active tip of the Hydrogen Abstraction Tool 100 which is used to selectively abstract a single hydrogen atom from a workpiece. Hydrogen Abstraction Tool 100 is shown prior to the abstraction of a hydrogen atom. The distal carbon atom 102 is a radical with a high affinity for hydrogen. Carbon atoms 102 and 104 are triply bonded to each other and in this and other structures are commonly referred to as "an ethynyl radical" or a "dimer." The ethynyl radical is bonded to carbon atom 106, called a "bridgehead" carbon atom. The remainder of the adamantane cage consists of 10 carbon atoms and the hydrogen atoms which terminate them.

In general use, the 6 carbon atoms at the base of the adamantane cage (i.e., the six carbon atoms in the adamantane cage most distant from carbon atom 106 in FIG. 1A) are bonded into an extended handle structure by which the tool is positioned.

The Hydrogen Abstraction Tool is used by positioning the whole tool, so that carbon atom 102 is in close proximity (e.g., one or two angstroms) to a hydrogen atom which is to be abstracted.

When the Hydrogen Abstraction Tool is so positioned, the selected hydrogen atom will bond more strongly to carbon atom 102 than to almost any other molecular structure and hence will transfer from that other structure to carbon atom 102. The Hydrogen Abstraction Tool 100 following a hydrogen abstraction will appear as a spent Hydrogen Abstraction Tool 110 shown in FIG. 1B, where the abstracted hydrogen 112 is shown bonded to carbon atom 102.

Figure 2:
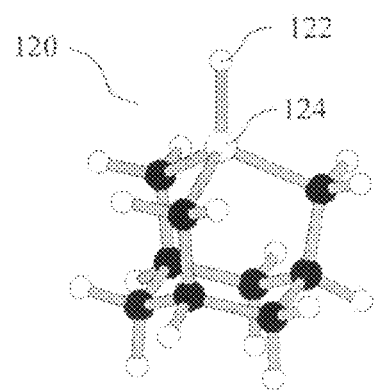
FIG. 2 is a Hydrogen Donation Tool.

(2) The Hydrogen Donation Tool. FIG. 2 illustrates the Hydrogen Donation Tool 120. The hydrogen atom 122 is bonded to germanium atom 124. Because the bond between germanium atom 124 and hydrogen atom 122 is not as strong as the bond that can be formed between hydrogen atom 122 and a carbon radical on a workpiece, the hydrogen atom 122 will, when positioned close to a carbon radical and with the application of mechanical force to overcome reaction barriers, transfer to that carbon radical and so donate a hydrogen to it.

Figure 3:
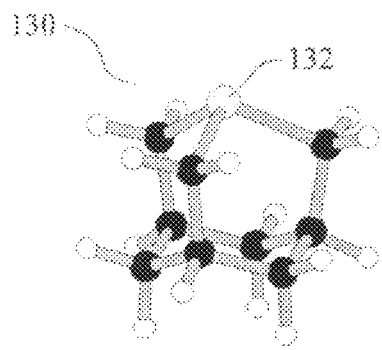
FIG. 3 is a Germanium Radical Tool.

(3) The Germanium Radical Tool. FIG. 3 illustrates the Germanium Radical Tool 130. The germanium atom 132 is a radical. The Germanium Radical Tool 130 results from the reaction that will occur when the Hydrogen Donation Tool 120 donates hydrogen atom 122 to a carbon radical.

Figure 4:
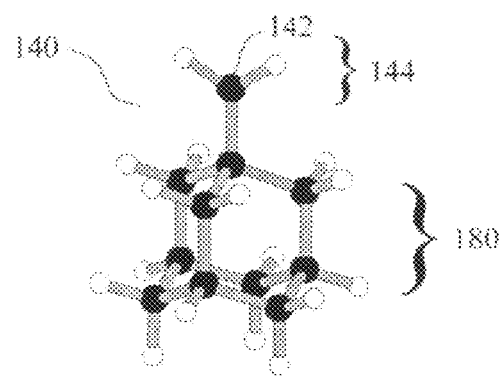
FIG. 4 is a Methylene Tool.

(4) The Methylene Tool. FIG. 4 illustrates the Methylene Tool 140. The Methylene Tool is formed by adding a $.CH_2$ group 144 to the Adamantane Radical Tool 180. The carbon atom 142 in $.CH_2$ group 144 is highly reactive because it is a radical.

Figure 5:
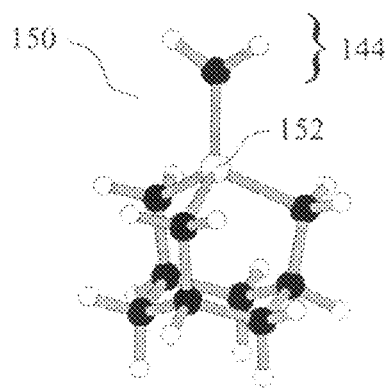
FIG. 5 is a GermylMethylene Tool.

(5) The GermylMethylene Tool. FIG. 5 illustrates the GermylMethylene Tool 150. Because the bond between $.CH_2$ group 144 and germanium atom 152 is relatively weak, the GermylMethylene tool can be used to transfer the $.CH_2$ group 144 to a carbon radical site on a growing workpiece.

Figure 6:
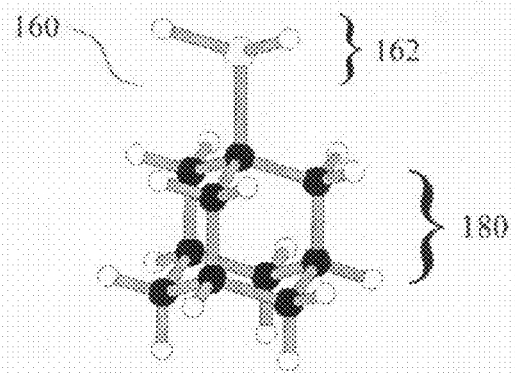
FIG. 6 is a Germylene Tool.

(6) The Germylene Tool. FIG. 6 illustrates the Germylene Tool 160 which can be formed by adding a $.GeH_2$ group 162 to the Adamantane Radical Tool 180. Germylene Tool 160 can be used in reaction sequences that add a germanium atom to a workpiece (and in particular, can be used during the synthesis of the Germanium Radical Tool 130).

Figure 7:
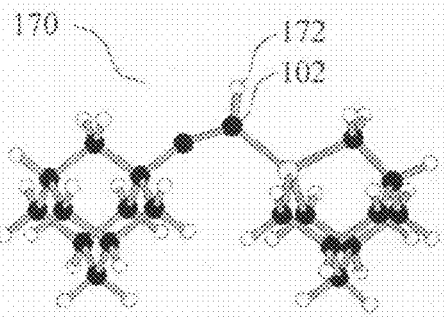
FIG. 7 is a Hydrogen Transfer Tool.

(7) The Hydrogen Transfer Tool. FIG. 7 illustrates the Hydrogen Transfer Tool 170 which can be formed by the reaction shown in FIG. 12A. The Hydrogen Transfer Tool is particularly useful because the bond between carbon atom 102 and hydrogen atom 172 is particularly weak, making it an excellent hydrogen donation tool.

Figure 8:
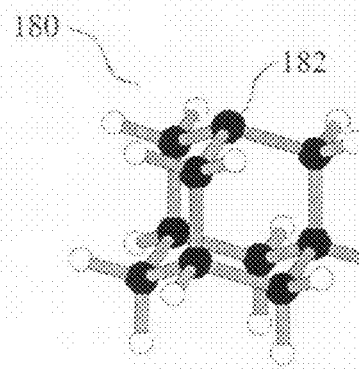
FIG. 8 is an Adamantane Radical Tool.

(8) The Adamantane Radical Tool. FIG. 8 illustrates the Adamantane Radical Tool 180 which can be formed by abstracting a hydrogen atom from an exposed adamantane cage on any diamond surface located, e.g., at the terminus of a tip, producing a single carbon radical 182.

Figure 9:
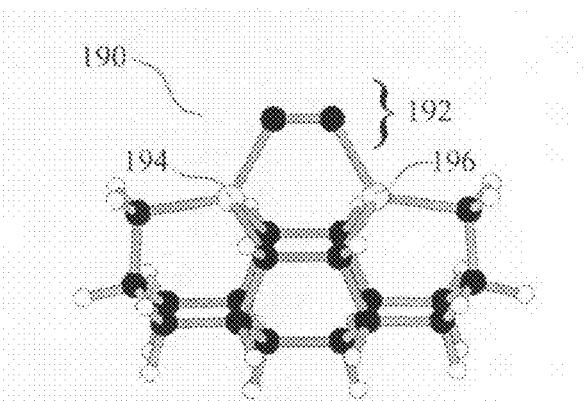
FIG. 9 is a Dimer Placement Tool.

(9) The Dimer Placement Tool. FIG. 9 illustrates the Dimer Placement Tool 190 in which a dimer 192 bonds to a tooltip which has two germanium atoms 194 and 196. The two bonds between the dimer 192 and the two germanium atoms 194 and 196 are highly strained, making the resulting Dimer Placement Tool 190 reactive and suitable for adding a dimer to a growing workpiece, particularly when two adjacent radical sites are present on the workpiece to which the dimer can bond.

These nine tools are used in an inert environment (e.g., ultra-high vacuum, a pressure of $10^{-9}$ torr ($10^{-12}$ atm) or less) and require that some suitable positional device be used to position the tools with high accuracy. In addition, there must be a source of feedstock molecules to provide the needed hydrogen, carbon and germanium atoms and optionally a sink for discard atoms if there is excess hydrogen.

One way to provide hydrogen is from a presentation surface covered by hydrogen atoms (e.g., a bulk produced flat hydrogenated diamond surface).

One way to provide carbon is in the form of $.CH_2$ groups distributed on a suitable presentation surface (e.g., on a bulk produced flat germanium surface). This also provides hydrogen, which may eliminate the need for an independent source for hydrogen.

One way to provide germanium is in the form of $.GeH_2$ groups distributed on a suitable presentation surface (e.g., on a bulk produced flat germanium surface).

Both carbon and germanium can also enter the system when provided as methyl or germyl groups ($CH_3$ or $GeH_3$) on a suitable presentation surface. In this case, they can be made chemically active by abstracting a hydrogen atom and converting them into $.CH_2$ or $.GeH_2$ groups respectively.

Excess hydrogen must be removed if, for example, the product structure being built has fewer hydrogen atoms than are present in the feedstock molecules, in which case, e.g., the excess hydrogen atoms provided by the $.CH_2$ groups must be disposed of. One way of doing this is to provide a surface to which the Hydrogen Donation Tool can donate hydrogen atoms. One such surface would be a bulk-produced atomically flat non-hydrogenated diamond surface.

These nine tools are used to carry out the various reactions needed to recharge themselves, to fabricate more tools, and to make other atomically precise structures (products).

Figure 10A:
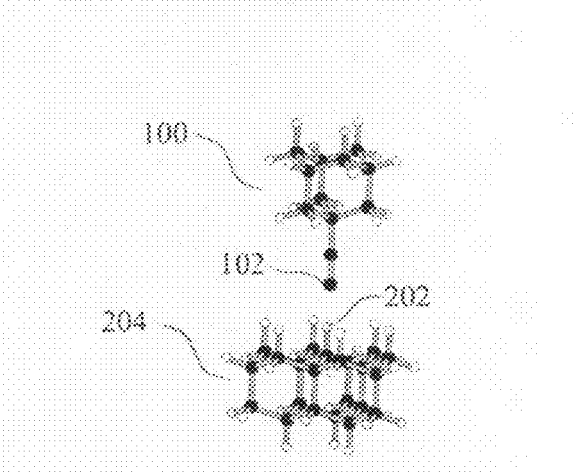
FIG. 10A shows a Hydrogen Abstraction Tool selectively abstracting a hydrogen atom.

Hydrogen Abstraction. FIG. 10A illustrates the use of the Hydrogen Abstraction Tool 100 to selectively abstract hydrogen atom 202. Hydrogen Abstraction Tool 100 is positioned so that radical carbon atom 102 is just above hydrogen atom 202 which is bonded to diamond surface 204. When Hydrogen Abstraction Tool 100 is brought into close proximity to diamond surface 204, the hydrogen atom 202 will bond to carbon atom 102, and thus transfer from diamond surface 204 to Hydrogen Abstraction Tool 100.

Figure 10B:
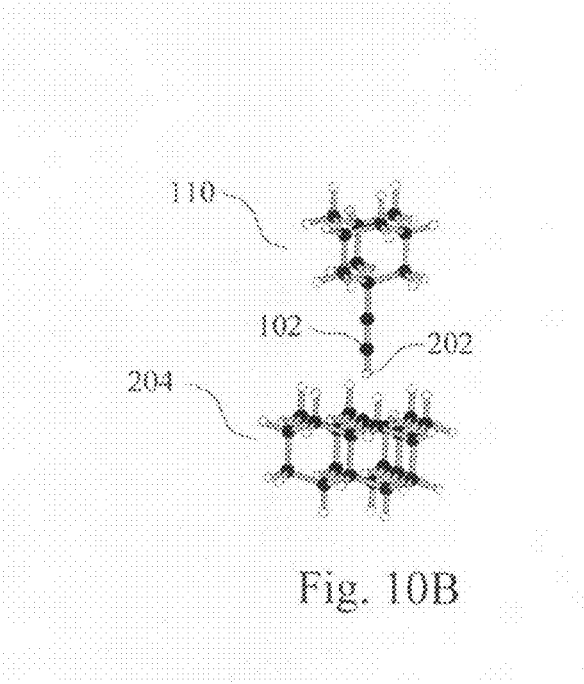
FIG. 10B shows abstraction in the transfer of a hydrogen atom and conversion to a spent Hydrogen Abstraction Tool.

FIG. 10B illustrates the result of the transfer of the hydrogen atom 202 to the Hydrogen Abstraction Tool 100 which serves to convert the Hydrogen Abstraction Tool 100 into a spent Hydrogen Abstraction Tool 110.

Hydrogen Donation. In one embodiment, a reaction sequence transfers a hydrogen atom from a Hydrogen Donation Tool to a diamond surface, both hydrogenating the radical site on the diamond surface and converting the Hydrogen Donation Tool to a Germanium Radical tool.

Figure 11A:
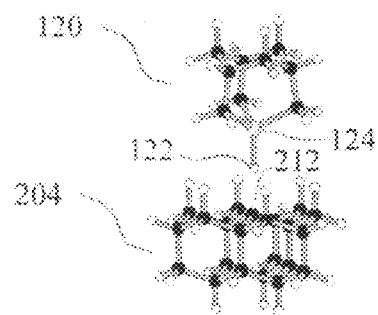
FIG. 11A shows a Hydrogen Donation Tool selectively donating a hydrogen atom.

FIG. 11A illustrates the use of the Hydrogen Donation Tool 120 to selectively donate one hydrogen 122 atom to carbon radical 212 on diamond surface 204. The Hydrogen Donation Tool 120 can be positioned directly above diamond surface 204 proximally close to carbon radical 212. When Hydrogen Donation Tool 120 is brought into close proximity to diamond surface 204 such that the attractive force between hydrogen atom 122 and carbon radical 212 exceeds the attractive force between the hydrogen atom 122 and the germanium atom 124, the hydrogen atom 122 will transfer from the germanium atom 124 and bond to the diamond surface 204 at the site of the carbon radical 212.

Figure 11B:
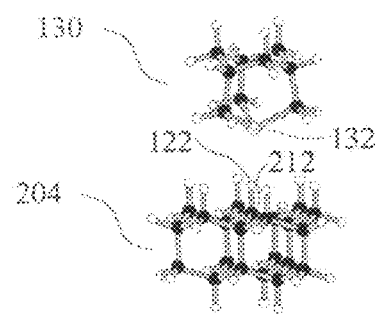
FIG. 11B shows the donation of a hydrogen atom and conversion to a Germanium Radical Tool.

FIG. 11B illustrates the result of the transfer of the hydrogen atom 122 to carbon atom 212 (now no longer a radical), which serves to convert the Hydrogen Donation Tool 120 into a Germanium Radical Tool 130 now having a germanium radical 132.

Recharge of Hydrogen Abstraction and Hydrogen Donation Tools. In one embodiment, a reaction sequence refreshes a Hydrogen Abstraction Tool by transferring a hydrogen atom from a spent Hydrogen Abstraction Tool to a Germanium Radical Tool.

Figure 12A:
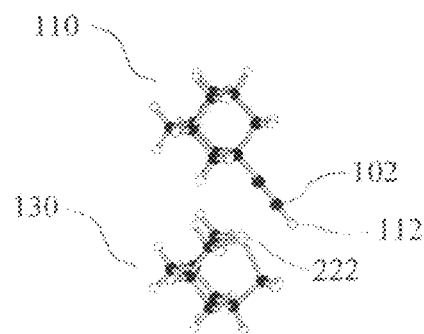
FIG. 12A shows a Germanium Radical Tool bonding to a spent Hydrogen Abstraction Tool.

FIG. 12A illustrates a Germanium Radical Tool 130 and a spent Hydrogen Abstraction Tool 110 with distal carbon atom 102 bonded to hydrogen atom 112. The spent Hydrogen Abstraction Tool is then brought into proximity to the Germanium Radical Tool 130 so that germanium radical 222 bonds to carbon atom 102 of spent Hydrogen Abstraction Tool 110. The result of the reaction is illustrated in FIG. 12B.

Figure 12B:
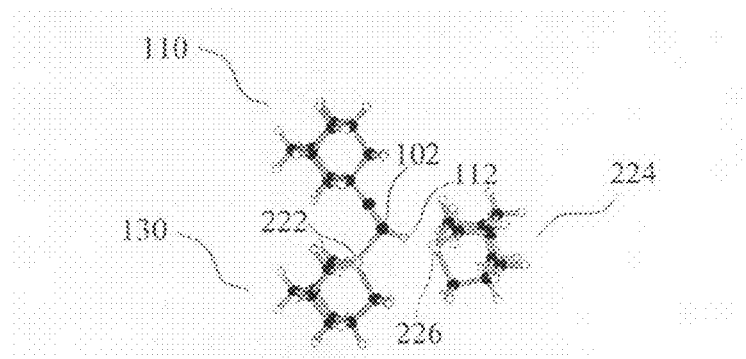
FIG. 12B shows a Germanium Radical Tool weakly bonded to a spent Hydrogen Abstraction Tool.

FIG. 12B illustrates the germanium radical 222 of the Germanium Radical Tool bonded to the distal carbon of the spent Hydrogen Abstraction Tool 110 in which hydrogen atom 112 is weakly bonded to carbon atom 102, along with a second (unbonded) Germanium Radical Tool 224. When the second Germanium Radical Tool 224 is positioned in close proximity to hydrogen atom 112 the hydrogen atom 112 debonds from carbon atom 102 and bonds to the germanium radical 226 of the second Germanium Radical Tool 224, thereby converting the second Germanium Radical Tool 224 into a Hydrogen Donation Tool. The result of the reaction is illustrated in FIG. 12C.

Figure 12C:
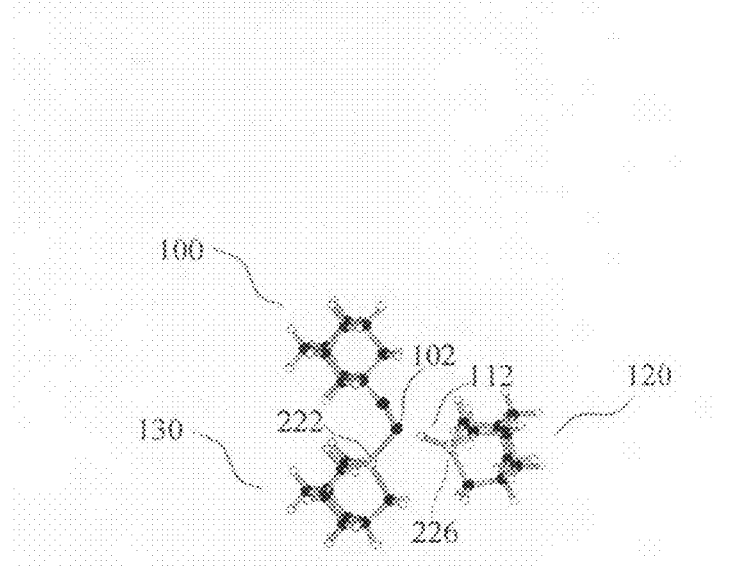
FIG. 12C shows a Germanium Radical Tool breaking bond to spent Hydrogen Abstraction Tool.
Figure 12D:
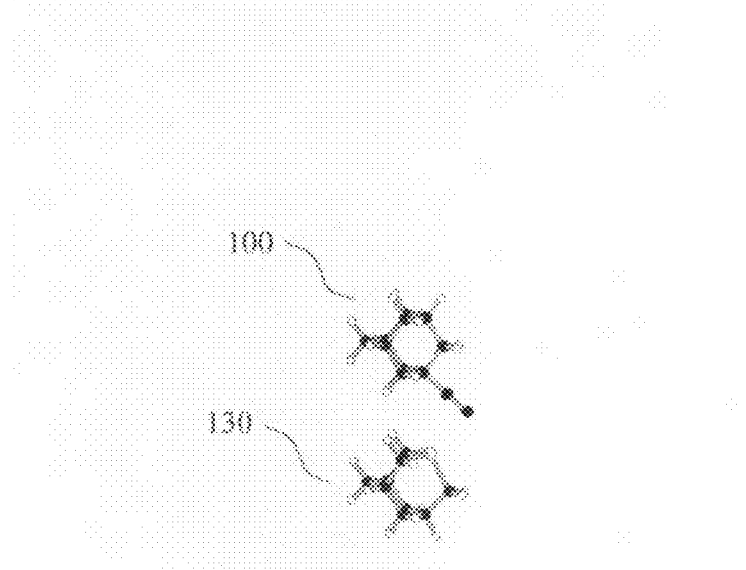
FIG. 12D shows a refreshed Hydrogen Abstraction Tool.

FIG. 12C illustrates the germanium radical 222 of the first Germanium Radical Tool 130 bonded to the distal carbon 102 of the Hydrogen Abstraction Tool 100, along with the resulting Hydrogen Donation Tool 120. When the first Germanium Radical Tool 130 is withdrawn by sufficient applied force from the Hydrogen Abstraction Tool 100, the bond between germanium atom 222 at the tip of the first Germanium Radical Tool 130 and carbon atom 102 at the tip of the Hydrogen Abstraction Tool 100 will break. The result of this mechanosynthetic reaction is illustrated in FIG. 12D, which shows the resulting refreshed Hydrogen Abstraction Tool 100 and recovery of the original Germanium Radical Tool 130 unchanged.

During mechanosynthesis, as many hydrogen atoms as desired can be added by abstracting hydrogen atoms from some convenient source (e.g., a hydrogenated diamond surface) using the Hydrogen Abstraction Tool, and then transferring the hydrogen atoms so obtained to Hydrogen Donation Tools from which they can be added to a workpiece. The reverse of this process can be used to get rid of excessive hydrogen atoms by donating them to a convenient sink (e.g., a non-hydrogenated diamond surface) using a Hydrogen Donation Tool. Consequently, the sequence described above can accommodate the net addition or removal of hydrogen atoms.

Charging the GermylMethylene Tool. The discharge of a GermylMethylene Tool creates a spent GermylMethylene Tool, which is identical to a Germanium Radical Tool. A GermylMethylene Tool can be charged by starting with a Germanium Radical Tool and .$CH_2$ groups distributed on a suitable presentation surface (e.g., germanium). The Germanium Radical Tool is touched to a .$CH_2$ group on the presentation surface, and then withdrawn. Although the .$CH_2$ group is bonded to a germanium atom on the presentation surface and to a germanium atom on the tip of the Germanium Radical Tool, the bond to the germanium atom on the tip of the Germanium Radical Tool is stronger (the germanium on the tip of the Germanium Radical Tool is in a different atomic bonding environment than the germanium on the presentation surface—in particular, it is bonded to 3 carbon atoms rather than being bonded to other germanium atoms).

Upon withdrawal of the tool handle from the presentation surface, the .$CH_2$ group is withdrawn with it, thus converting the Germanium Radical Tool back into a GermylMethylene Tool, completing the recharge process.

Methylation of a Selected Site on a Diamond Workpiece. FIGS. 13A-E illustrate mechanosynthetic methylation of a selected atomic site. During fabrication, workpieces will frequently be hydrogenated to eliminate dangling bonds and to avoid unexpected reconstructions. Some of these hydrogenations, particularly when immediately followed by hydrogen abstraction, can simply be omitted. Because of this general assumption, the first step in the methylation sequence is to abstract a hydrogen atom from the specific site to allow addition of a $CH_3$ group. When this general assumption is not used (i.e., when exposed radical sites are not immediately hydrogenated) there might be multiple radical sites available on the workpiece that could be methylated without first abstracting a hydrogen. In such cases, the step illustrated in FIG. 13A in the following sequence could be eliminated, and steps illustrated in FIG. 13D and FIG. 13E might also be eliminated if there is no immediate need to hydrogenate this particular added .$CH_2$ group, leaving only steps illustrated in FIG. 13B and FIG. 13C as required for this method. The need (or lack thereof) for hydrogenation or dehydrogenation in a given case will be readily apparent to a practitioner skilled in the art.

Figure 13A:
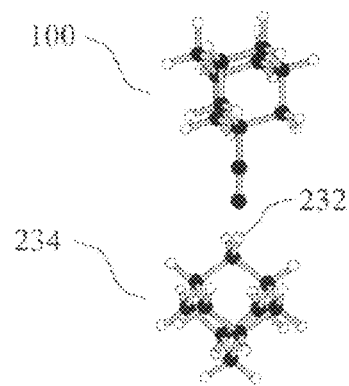
FIG. 13A shows abstracting hydrogen from a workpiece.

FIG. 13A illustrates abstracting the hydrogen atom 232 that occupies the site where the methyl group is to be placed. Hydrogen Abstraction Tool 100 abstracts hydrogen atom 232 from adamantane cage 234, which represents a few atoms from a larger diamond workpiece.

Figure 13B:
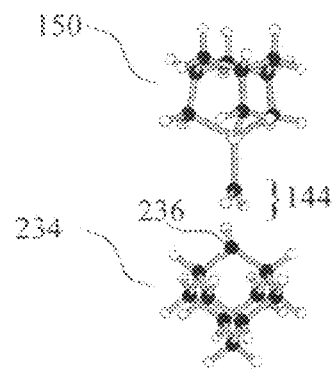
FIG. 13B shows a GermylMethylene Tool being position in close proximity to a radical carbon atom.

FIG. 13B illustrates GermylMethylene Tool 150 being positioned so that .$CH_2$ group 144 is in close proximity to radical carbon atom 236. With the application of mechanical force to overcome reaction barriers, the .$CH_2$ group 144 will then bond to radical carbon atom 236 as shown in FIG. 13C, the next step in the sequence.

Figure 13C:
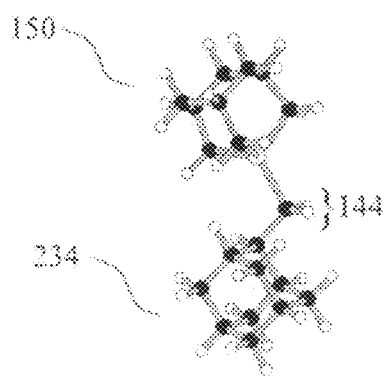
FIG. 13C shows a GermylMethylene Tool bonded to a $CH_2$ group.

FIG. 13C illustrates the GermylMethylene Tool 150 bonded to the .$CH_2$ group 144. The GermylMethylene Tool 150 is withdrawn by the application of mechanical force, converting GermylMethylene Tool 150 into a Germanium Radical Tool (not shown) and the .$CH_2$ group is left behind on the workpiece 234.

Figure 13D:
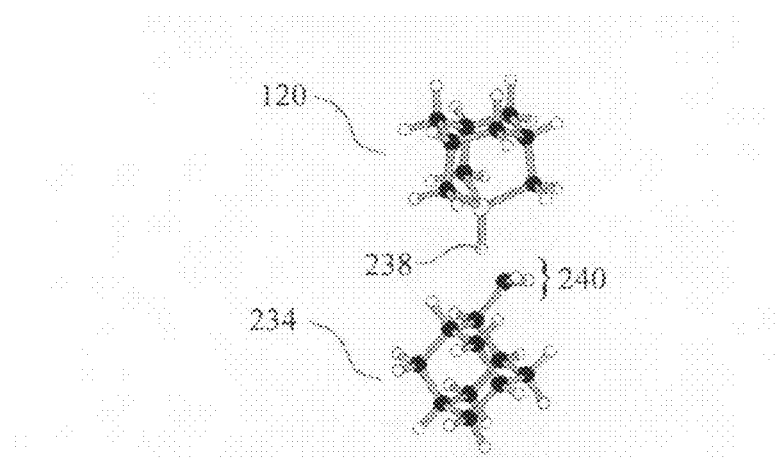
FIG. 13D shows a Hydrogen Donation Tool positioned to donate a hydrogen atom to the $CH_2$ group.

FIG. 13D illustrates a Hydrogen Donation Tool 120 which is positioned to donate hydrogen atom 238 to the radical site on the .$CH_2$ group 240. With the application of mechanical force to overcome reaction barriers, hydrogen atom 238 is bonded to the .$CH_2$ group 240.

Figure 13E:
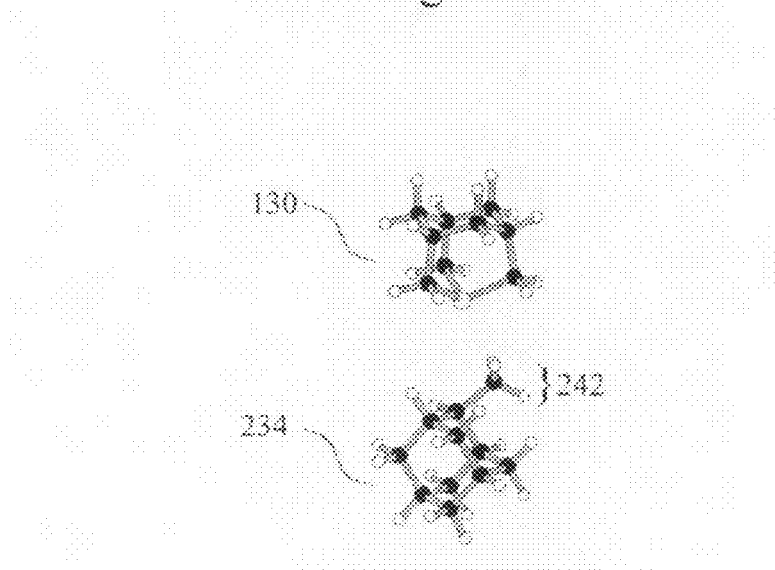
FIG. 13E shows hydrogen transferred to radical site on $CH_2$ group and a Hydrogen Donation Tool converted into a Germanium Radical Tool.

FIG. 13E illustrates the result of the reaction in which the hydrogen on the Hydrogen Donation Tool has been transferred to the radical site on .$CH_2$ group 240, converting it to $CH_3$ group 242. The Hydrogen Donation Tool is converted by this process into Germanium Radical Tool 130.

This reaction sequence provides a specific example of a more general method. This method can be applied to add a methyl group to virtually any exposed carbon radical on any hydrocarbon structure. It can also be used to add a methyl group to a wide range of other possible target structures.

Ring Closure on a Diamond Workpiece. The addition of individual methyl groups is very powerful, and in conjunction with the ability to close a ring, provides a mechanism for fabricating a wide range of diamond and diamond-like structures.

Figure 14A:
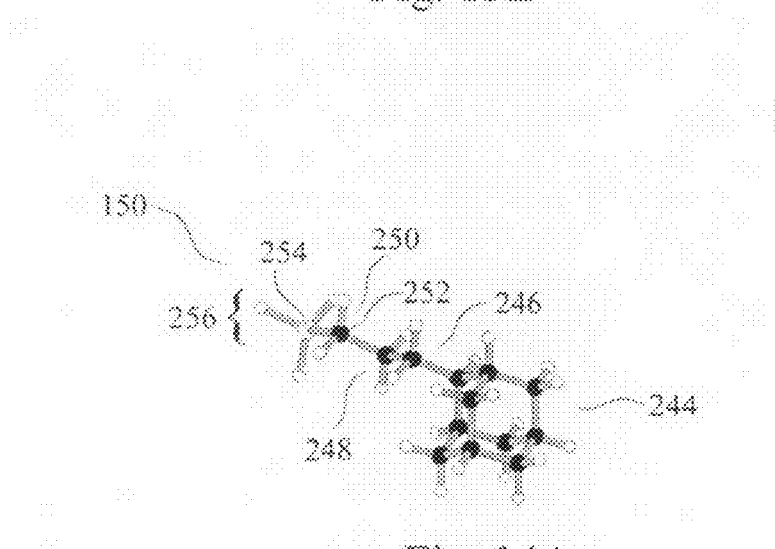
FIG. 14A shows a GermylMethylene Tool bonded to the third methylene group of a chain of three methylene groups that has been bonded to an adamantane workpiece.

FIG. 14A illustrates a structure to which three $CH_2$ groups have already been added. The first $CH_2$ group 246 is attached to a sidewall site on adamantane cage 244, a cage that represents a few atoms from a larger diamond workpiece. The second $CH_2$ group 248 is added to the first $CH_2$ group 246, and the third $CH_2$ group 250 is added to the second $CH_2$ group 248. The GermylMethylene Tool 150 that is used to add the third $CH_2$ group 250 (thus incorporating the final carbon atom 252 in the chain) is not withdrawn, but instead is left attached so that this tool can be used to re-position carbon atom 252. For purposes of brevity of illustration only, the GermylMethylene Tool 150 is represented by a single germanium atom 254 and 3 attached hydrogen atoms 256, rather than the full adamantane cage structure of the GermylMethylene Tool 150 as shown in FIG. 5.

Figure 14B:
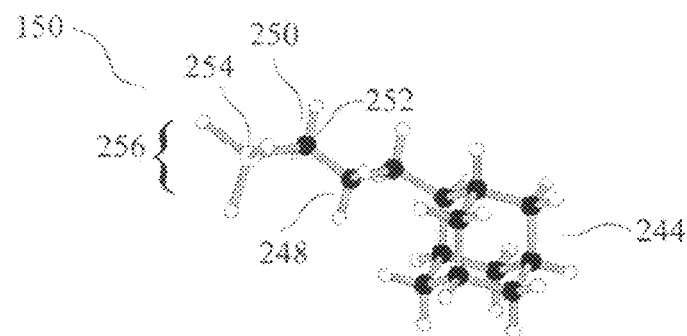
FIG. 14B shows the third methylene group rotated to a different position relative to the chain of three methylene groups attached to an adamantane workpiece, using a GermylMethylene Tool.

FIG. 14B illustrates the structure that results after $CH_2$ group 250 has been rotated from the trans to the cis configuration relative to $CH_2$ group 248, which is accomplished by the application of lateral forces transmitted through the handle of the attached GermylMethylene Tool 150.

Figure 14C:
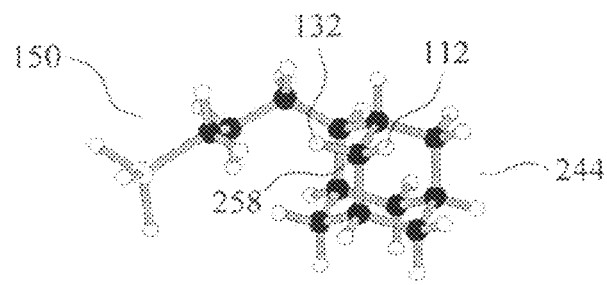
FIG. 14C shows the chain of three methylene groups rotated into a cagelike configuration relative to an adamantane workpiece, using a GermylMethylene Tool bonded to the third methylene group in the chain of three methylene groups.

FIG. 14C illustrates the structure that results after $CH_2$ group 248 has been further rotated relative to $CH_2$ group 246 such that the three $CH_2$ groups 246, 248 and 250 are re-oriented into a cage-like configuration relative to the workpiece; this re-orientation is accomplished by the application of lateral forces transmitted through the handle of the attached GermylMethylene Tool 150. FIG. 14C also shows the location of hydrogen atom 132 that will be abstracted in the next reaction step, and the location of hydrogen atom 112 that will be abstracted in the next reaction step after that.

Figure 14D:
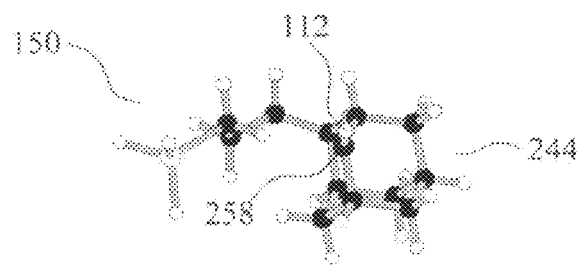
FIG. 14D shows the configuration of FIG. 14C after a first hydrogen atom has been abstracted from a sidewall carbon atom of the adamantane workpiece.

FIG. 14D illustrates the workpiece 244 after the abstraction of hydrogen atom 132 from carbon atom 258. FIG. 14D also shows the location of hydrogen atom 112 that will be abstracted in the next reaction step.

Figure 14E:
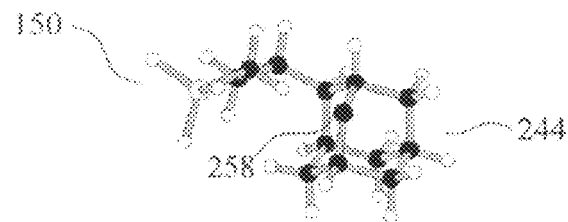
FIG. 14E shows the configuration of FIG. 14D after a second hydrogen atom has been abstracted from the same sidewall carbon atom of the adamantane workpiece.

FIG. 14E illustrates the workpiece 244 after the abstraction of a second hydrogen atom 112 from the same carbon atom 258, which becomes a carbene diradical. The two hydrogen abstractions that occur in FIG. 14D and FIG. 14E are not shown explicitly but require the use of two Hydrogen Abstraction Tools in the abstraction process.

Figure 14F:
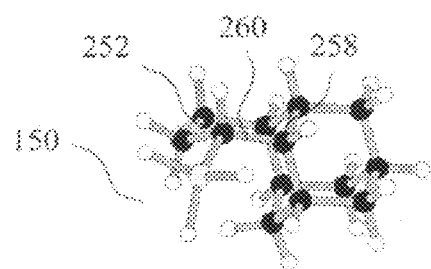
FIG. 14F shows the chain of three methylene groups bonded to a sidewall carbon atom of the adamantane workpiece, thus closing a ring of three methylene groups, with the GermylMethylene Tool still attached.

FIG. 14F illustrates GermylMethylene Tool 150 being positioned so that carbene 258 inserts into the CH bond between carbon atom 252 and one of its attached hydrogen atoms with the application of mechanical force. Following this insertion reaction, carbon atom 252 will bond to carbon atom 258 via bond 260.

Figure 14G:
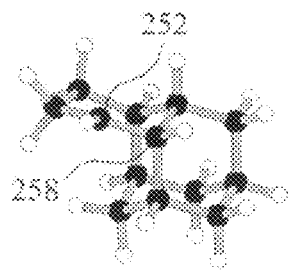
FIG. 14G shows the configuration of FIG. 14F after the GermylMethylene Tool is detached.

FIG. 14G illustrates the workpiece after the GermylMethylene Tool 150 is withdrawn, leaving carbon atom 252 attached to carbon atom 258. Carbon atom 252 is now, because of the withdrawal of GermylMethylene Tool 150, a radical.

Figure 14H:
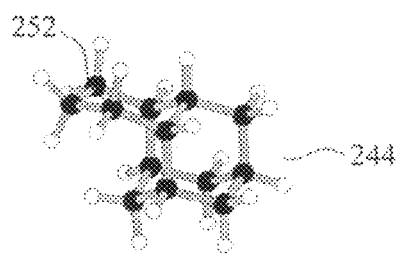
FIG. 14H shows the adamantane workpiece with a fully passivated three-methylene ring attached between two sidewall sites.

FIG. 14H illustrates the state after the final step in the mechanosynthetic reaction sequence which is to hydrogenate the radical site at carbon atom 252 using a Hydrogen Donation Tool 120 (not shown). The donation reaction, which requires the application of mechanical force to overcome a reaction barrier, is not shown explicitly but requires the use of a Hydrogen Donation Tool. Following this hydrogenation, carbon atom 252 has four bonds, two bonds to adjacent carbon atoms and two bonds to hydrogen atoms. This mechanosynthetic reaction sequence results in a closed chain of 3 carbon atoms (derived from $CH_2$ groups 246, 248 and 250) being added to workpiece 244.

GermylMethylene Tool 150 must be positionally rotated during this sequence. An alternative method of changing the orientation of GermylMethylene Tool 150 is to perform a handle exchange, substituting a new tool in a new orientation for the existing GermylMethylene Tool 150. In this alternative method, a hydrogen atom is first abstracted from $CH_2$ group 250 at the tip of the attached GermylMethylene Tool 150, creating a radical site at carbon atom 252 to which a new Germanium Radical Tool which is already in the desired new orientation (and precisely positioned in X, Y and Z) can next be bonded. Following this bonding, withdrawal of the GermylMethylene Tool 150 leaves the carbon atom 252 bonded to the new Germanium Radical Tool (not shown in this figure). The radical carbon atom 252 is then hydrogenated with an additional Hydrogen Donation Tool (not shown in this figure). This process effectively performs a handle exchange, with the new handle in a different orientation. This avoids the need to manipulate a single handle and change its orientation while it is attached to the workpiece, simplifying the positioning required during the ring-closing reaction sequence described above.

While the above described method of creating a ring is very flexible, it is possible to fabricate diamond using simpler methods in some cases. In particular, in the case of mechanosynthetic manufacture of the C(110) diamond surface, methyl groups can be added on top of the troughs on the C(110) surface and then cross-bonded. This process described in more detail below (and illustrated in FIG. 19) in the context of fabricating a simple handle structure during a bootstrap process.

Building Tool Handles. Once the ability to fabricate diamond and similar hydrocarbons is achieved (using the ring closure reaction as described above, or using methylation of a C(110) diamond surface as described below, or using other reactions that would readily be apparent to someone skilled in the art and having the benefit of the teachings presented herein), atomically precise handle structures can readily be fabricated that will be suitable for supporting the various tooltips illustrated in FIGS. 1-9.

Figure 1B:
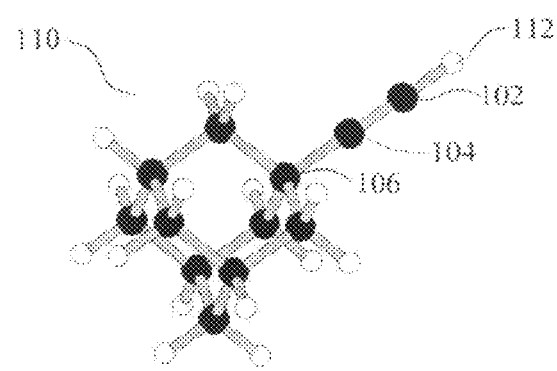
FIG. 1B is a spent Hydrogen Abstraction Tool.

Building Specific Tools. Given a toolset with a sufficient number of each type of tool, it is possible to build more of any of the nine tools. Once having built a suitable handle structure, the specific tooltip can be added. Reviewing the tools in order:

(1) Hydrogen Abstraction Tool. Having built the handle and the adamantane cage at the apex of the handle, we then add a methyl group at the tip, followed by adding a second methyl group to the first methyl group. All but one of the hydrogen atoms on these two methyl groups are then be abstracted using other Hydrogen Abstraction Tools, creating the Hydrogen Abstraction Tool in its spent version (as shown in FIG. 1B). This structure is then refreshed using the Hydrogen Abstraction Tool recharge sequence shown in FIG. 12.

(2) Hydrogen Donation Tool. We use a Germanium Radical Tool in the Hydrogen Abstraction Tool recharge sequence shown in FIG. 12 to convert the Germanium Radical Tool to a Hydrogen Donation Tool.

(3) Germanium Radical Tool. Having built the handle, we use the Germylene Tool to add the single germanium atom needed at the tip of this tool. The use of hydrogen gas to hydrogenate a germanium diradical during synthesis of the Germanium Radical Tool can be omitted without ill effect. In many cases, a reaction sequence specifies hydrogenation of intermediate structures as part of a conservative strategy to insure their stability, even when the need for such hydrogenation might otherwise not be clear.

(4) Methylene Tool. Starting with the Adamantane Radical Tool, we bond the Adamantane Radical Tool to a $.CH_2$ group on a suitable presentation surface (e.g., germanium) and retract the tool producing a Methylene Tool.

(5) GermylMethylene Tool. Starting with the Germanium Radical Tool, we bond the Germanium Radical Tool to a $.GeH_2$ group on a suitable presentation surface (e.g., germanium). The reaction energetics favor transfer of the $.GeH_2$ group to the tooltip from a germanium presentation surface. We then retract the tool, producing a GermylMethylene Tool.

(6) Germylene Tool. Starting with the Adamantane Radical tool, we bond the Adamantane Radical Tool to a $.GeH_2$ on a suitable presentation surface (e.g., germanium) and retract the tool, producing a Germylene Tool.

Figure 15A:
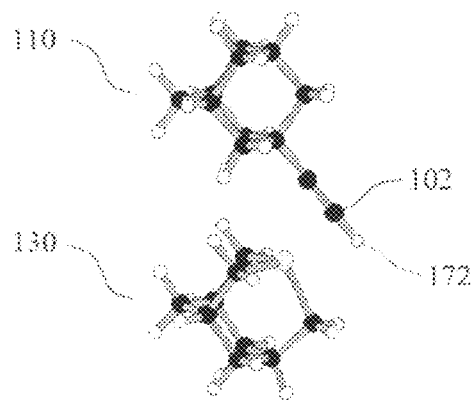
FIG. 15A shows a Germanium Radical Tool bonded to a spent Hydrogen Abstraction Tool.
Figure 15B:
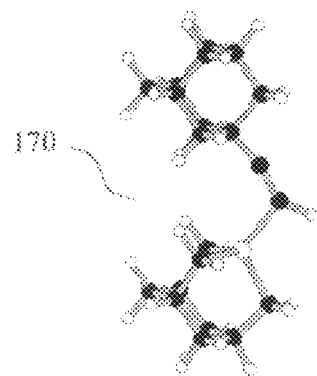
FIG. 15B shows a resulting Hydrogen Transfer Tool.

(7) Hydrogen Transfer Tool. Starting with a spent Hydrogen Abstraction Tool and a Germanium Radical Tool as shown in FIG. 15A, Germanium Radical Tool 130 is bonded to the distal carbon atom 102 of the spent Hydrogen Abstraction Tool 110 yielding Hydrogen Transfer Tool 170 as shown in FIG. 15B.

(8) Dimer Placement Tool. After fabricating a first Germanium Radical Tool, a second Germanium Radical Tool is constructed in a lonsdaleite polytype configuration on the side of the first Germanium Radical Tool, yielding a discharged Dimer Placement Tool which is then recharged with $C_2$ dimer by the addition of two carbon atoms using two GermylMethylene Tools, followed by the abstraction of four hydrogen atoms using four applications of Hydrogen Abstraction Tools.

(9) Adamantane Radical Tool. Using the Hydrogen Abstraction, Hydrogen Donation and GermylMethylene Tools, we can build the handle structure for the Adamantane Radical Tool and the Adamantane Radical Tool itself.

Given enough Hydrogen Abstraction Tools and Hydrogen Donation Tools, we can build a limited number of Germanium Radical Tools (limited by the number of Hydrogen Donation Tools) by using the Hydrogen Donation Tools to donate hydrogen atoms to a hydrogen dump (e.g., a non-hydrogenated diamond surface). With these Germanium Radical Tools we can build and recharge GermylMethylene Tools (given the availability of a suitable presentation surface for $.CH_2$ groups). Using these tools, and recharging the tools as needed, we can then build as many Hydrogen Abstraction Tools and as many Adamantane Radical Tools as desired (these tools are made from carbon and hydrogen only, and have no germanium).

With the availability of a suitable presentation surface for $.CH_2$ groups, the Adamantane Radical Tools can be charged with $.CH_2$ groups, producing as many Methylene Tools as desired.

With the availability of a suitable presentation surface for $.GeH_2$ groups, the Adamantane Radical Tools can be charged with $.GeH_2$ groups, producing as many Germylene Tools as desired.

The Germylene Tools, along with the previously available tools, then let us make as many Germanium Radical Tools as desired, which in turn allow us to make as many GermylMethylene Tools and as many Hydrogen Donation Tools as desired. Combining spent Hydrogen Abstraction Tools and Germanium Radical Tools lets us make as many Hydrogen Transfer Tools as desired. Finally, we can make as many Dimer Placement Tools as desired using the previous tools.

Although the present invention has been described in considerable detail with reference to certain preferred versions thereof, other versions are possible. For example, having fabricated a sufficient number of rechargeable atomically precise tools, reaction sequences allow the fabrication of a wide range of atomically precise diamondoid and graphene structures, permits further expansion of the toolset to include elements other than carbon, germanium, and hydrogen, and also permits expansion of the reaction set to include alternative or additional reactions, reaction sequences, feedstock molecules, presentation surfaces, and toolsets. Therefore, the scope of the appended claims should not be limited to the description of the preferred versions contained herein.

Introduction to the Bootstrap Process. The present invention describes a set of nine molecular tools sufficient to make additional sets of the self-same tools as described above. These tools are illustrated in FIGS. 1-9. Given an adequate initial number of each of these nine tools, with the tools being positionally controlled by suitable positional devices and given suitable presentation surfaces for feedstock molecules, it is possible to build additional sets of the self-same tools.

The first toolset, however, must be built without the benefit of a previously existing toolset. Thus this first toolset must be fabricated from simpler proto-tools that can be fabricated using known methods that are experimentally accessible. Once such a bootstrap process has been executed, yielding a first set of tools in small but adequate numbers, the bootstrap process need not be repeated again. Hence each reaction sequence comprising the bootstrap process need only be carried out a small number of times. As a consequence, any methods (even expensive ones) of building the first set of tools are sufficient to enable the fabrication of more tools. These methods can be carried out at low temperature (e.g., 80 K is readily available using liquid nitrogen, 4 K using liquid helium) and by the use of proto-tools having only modest reliability. Reducing the temperature dramatically increases the number of reliable operations that are available for use during the bootstrap sequence using proto-tools, even if the resulting more sophisticated final toolset (that is fabricated by the proto-tools) is intended for eventual use at a higher temperature.

It is possible to make the complete set of nine tools given only the Hydrogen Abstraction and Hydrogen Donation Tools. With a small but adequate initial supply of these two tools—when operated with appropriate positional control in an inert environment, and when provided with a source of feedstock molecules (e.g., $.CH_2$, $.GeH_2$ and H distributed on appropriate presentation surfaces) and a hydrogen dump (a surface with a high affinity for hydrogen on which excess hydrogen would be placed, e.g., bulk-produced atomically flat clean diamond)—it is possible to manufacture additional instances of all nine tools.

Therefore, for one preferred embodiment of a representative bootstrap process, proto-tools are fabricated that are the functional equivalent of the Hydrogen Abstraction and Hydrogen Donation Tools. There are many possible bootstrap sequences depending on the toolset, on the particular method of selecting an initial subset of the tools, and on the particular method of creating functional equivalents of those initial tools using existing technology. The particular sequence described here, which is but one of many possible sequences, employs existing ultrasharp silicon and diamond SPM tips. While atomically precise tips will likely be required for the ultimate in high reliability operation at ambient temperatures, current ultrasharp scanning probe tips having nanometer or sub-nanometer radius of curvature when operated at low temperature are sufficient for the more modest reliability requirements of a bootstrap sequence. Such ultrasharp scanning probe tips are commercially available, e.g., silicon tips with tip radii of 2 nm or less, and diamond-like carbon (DLC) spike-probe tips having a sub-nanometer asperity that is only a few carbon atoms wide at its distal terminus.

The bootstrap process often employs the following general principle: one or more atoms are driven "downhill" in energy as they are transferred from the feedstock molecule presentation surface, to the tip, and finally to the workpiece, with atomic affinity increasing as the reaction sequence progresses.

Implementing this general principle proceeds in the following stages:

(1) Distribute desired feedstock molecules onto a presentation surface. While these feedstock molecules bond more weakly to the surface than to the tip (making it easy to acquire the feedstock molecules with the tip) the feedstock molecules bond strongly enough to prevent them from migrating upon or departing from the presentation surface at the designated operating temperature.

(2) If necessary, activate one of the feedstock molecules (e.g., by abstracting a hydrogen atom and making it reactive, once the first hydrogen abstraction tool is available).

(3) Bring a tip (positioned by an SPM-like apparatus or some other positional device) into contact with the activated feedstock molecule, and bond to it with the tip, possibly requiring the application of mechanical force to overcome reaction barriers. This tip might or might not be atomically precise. The resulting newly formed bond is stronger than the bond that holds the feedstock molecule to the presentation surface.

(4) Withdraw the tip, and with it withdraw the transferred feedstock molecule from the presentation surface.

(5) Use the SPM tip to position the transferred molecule next to a workpiece, possibly requiring the application of mechanical force to overcome reaction barriers. For an appropriately selected workpiece and feedstock molecule, the bond that forms between the workpiece and the cluster will be stronger than the bond between the cluster and tip.

(6) Withdraw the tip, leaving the transferred feedstock molecule behind on the workpiece.

If the presentation surface is germanium (which forms relatively weak bonds) and the feedstock molecule is $.CH_2$, $.GeH_2$ or even more simply just a single hydrogen atom H, then a silicon tip will bond to the cluster more strongly than the germanium surface. If the workpiece is a stiff hydrocarbon structure, the feedstock molecule (e.g., H, $.CH_2$, or $.GeH_2$) will bond more strongly to a radical carbon site on the workpiece than it would to the silicon tip, and so can be transferred to the workpiece at a desired location. That is, the feedstock molecule moves downhill in energy as it transfers from the presentation surface, to the tip, and finally to the workpiece.

Even when the bond strengths between the feedstock molecule, the presentation surface, the SPM tip and the workpiece are very similar (e.g., the energetics are close to level rather than downhill), the insertion of a sufficient number of test-and-repeat steps can be used to obtain adequately reliable results.

Lowering the temperature can also be used to remove the randomizing effect of thermal noise. At a sufficiently low temperature for a given reaction, thermal noise will no longer significantly disturb the outcome and the reliability of the operations is then limited by other factors.

Figure 16A:
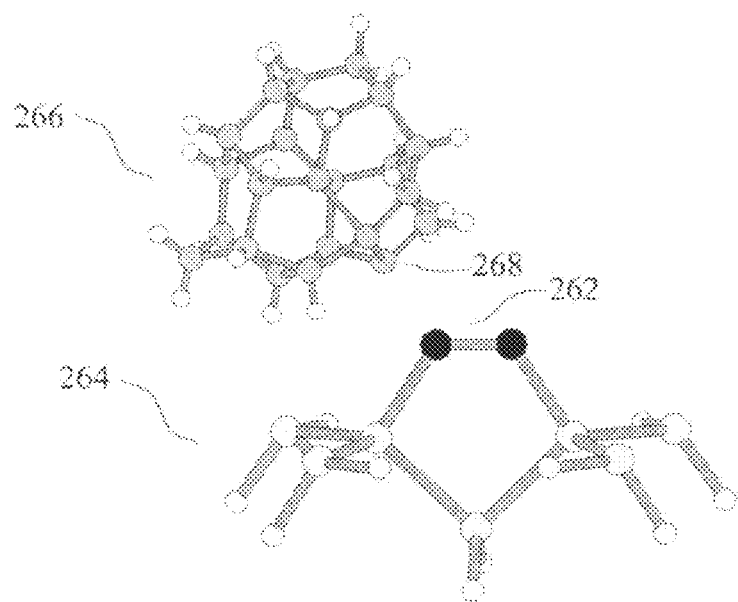
FIG. 16A shows a bootstrap sequence for a proto-Hydrogen Abstraction tip.

Starting a Bootstrap Sequence: the proto-Hydrogen Abstraction tip. FIG. 16A illustrates how a bootstrap sequence may start with the fabrication of a proto-Hydrogen Abstraction tip. The proto-Hydrogen Abstraction tip 270 (FIG. 16B) differs from the Hydrogen Abstraction Tool 100 (FIG. 1) in that the proto-Hydrogen Abstraction tip does not necessarily have an atomically precise adamantane cage at the base of the ethynyl radical. It should be understood that the particular proto-Hydrogen Abstraction tip 270 is but one instance of an entire class of structures that incorporates some degree of randomness in the fabrication process but which still has the requisite properties. For the proto-Hydrogen Abstraction tip it is sufficient that the ethynyl radical is in place and functions.

One method of preparing the first proto-Hydrogen Abstraction tip is by the following five-step sequence.

(1) $C_2$ dimers are chemisorbed onto an appropriate presentation surface. As illustrated in FIG. 16A, the preparation may begin with the direct chemisorption of $C_2$ dimers 262 onto a depassivated surface 264 which may be (among many other possibilities) either silicon or germanium.

(2) Having once obtained a suitable presentation surface with $C_2$ dimers distributed on it, a sub-nanometer radius diamond tip 266 is at least partially depassivated by any of several methods, which might include: (A) heating to an appropriate temperature (e.g., 700-800 K for diamond C(111) and C(100) surfaces), (B) contacting the tip to an already depassivated surface (e.g., a surface with an equal or higher affinity for hydrogen), or (C) by the standard practice of applying a suitable voltage pulse to cause removal of one or more hydrogen atoms from the tip. This produces at least one radical site 268 on the tip.

(3) The tip 266 is brought into contact with one end of a chemisorbed dimer 262, resulting in the dimer bonding to the tip, possibly requiring the application of mechanical force to overcome reaction barriers.

Figure 16B:
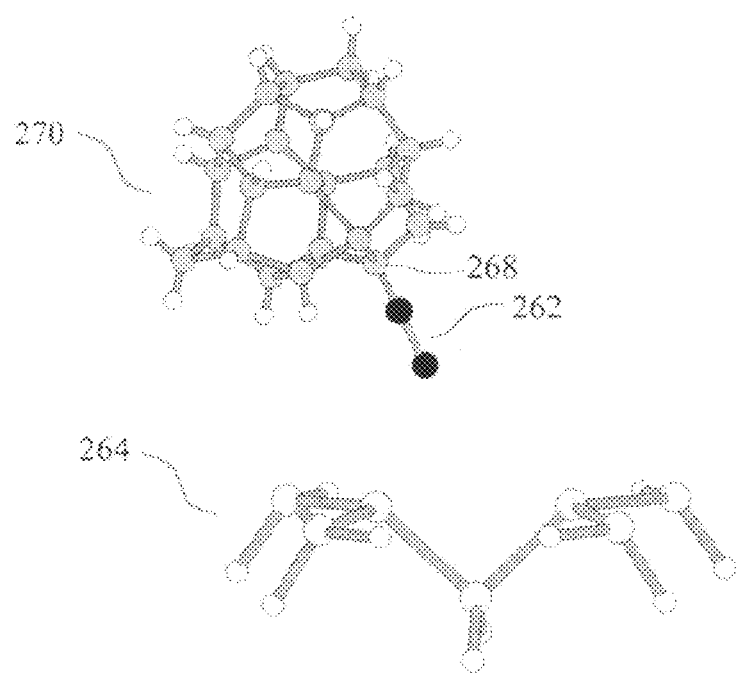
FIG. 16B shows the result when the proto-Hydrogen Abstraction tip is withdrawn from the presentation surface.

(4) The tip is then withdrawn from the presentation surface, producing the desired proto-Hydrogen Abstraction tip 270 as illustrated in FIG. 16B.

(5) A "test and repeat" step may be employed to ensure that the resulting proto-Hydrogen Abstraction tip has been made successfully, if increased reliability is desired.

The resulting proto-Hydrogen Abstraction tip can then be used to selectively abstract hydrogen in subsequent mechanosynthetic steps. In addition, the minimal toolset reactions normally required in the recharge sequence for the proto-Hydrogen Abstraction tip are avoided during the bootstrap sequence by discarding the proto-Hydrogen Abstraction tip after a single use and making additional proto-Hydrogen Abstraction tips as needed to abstract additional hydrogen atoms. While inefficient, this serves adequately to produce a sufficient (small) number of proto-Hydrogen Abstraction tips during the bootstrap process.

The proto-Silicon Hydrogen Donation tip. After creation of a proto-Hydrogen Abstraction tip, it is necessary to produce a proto-Hydrogen Donation tip. A functionally equivalent tool may substitute a silicon atom in place of germanium atom 124 in the Hydrogen Donation Tool illustrated in FIG. 2. Such a tool, which may be called a proto-Silicon Hydrogen Donation tip, will be effective at donating hydrogen atom 122 to a carbon radical on a diamond workpiece.

The most direct method for obtaining a proto-Hydrogen Donation tip is to create an ultrasharp hydrogenated germanium tip with <2 nm radius of curvature. Ultrasharp germanium tips are not yet commercially available, but ultrasharp silicon tips are commercially available and can also be used. The hydrogenated ultrasharp silicon tip is designated as a proto-Silicon Hydrogen Donation tip.

The primary reason for using germanium in the toolset rather than silicon is the higher reliability of operation with germanium. The substitution of a silicon tip for a germanium tip also works as required for the reactions needed during the bootstrap sequence. Silicon, being one row closer than germanium to carbon, has bond strengths to carbon atoms that are intermediate in strength between C—C bonds and C—Ge bonds. As a result the critical reactions used during the bootstrap sequence will work with silicon substituted for germanium but will have lower reliability at any given operating temperature. Lowering the temperature of operation recovers much of the foregone reliability. Thus the use of commercially available silicon tips with <2 nm radii will suffice because lower temperature operation during the bootstrap sequence is readily available, and because lower-reliability processes are tolerable during bootstrapping.

Proto-Hydrogen Abstraction tips and proto-Silicon Hydrogen Donation tips are then used to fabricate the rest of the tips in the bootstrap process, followed by all the tools in the minimal toolset, as described below.

The proto-Silicon Radical tip. By touching the proto-Silicon Hydrogen Donation tip to the hydrogen dump (which, among other possibilities, can be a simple dehydrogenated bulk but atomically flat diamond surface) a hydrogen atom is donated from the proto-Silicon Hydrogen Donation tip to the diamond surface, thus creating a radical site on the tip. The resulting tip is designated as a proto-Silicon Radical tip. This provides the functionality of the Germanium Radical Tool for some or all of the bootstrap sequence.

The proto-Silicon Radical tip also may be fabricated by abstracting a hydrogen atom from the proto-Silicon Hydrogen Donation tip using the proto-Hydrogen Abstraction tip.

More generally, a wide range of possible proto-radical tips may be used, and there are many methods of manufacturing any particular instance of such a tip, as for example: (1) heating a workpiece diamond, silicon or germanium tip to a temperature sufficient to drive off some of the hydrogen atoms on the tip (e.g., 700-800 K for diamond C(111) and C(100) surfaces), (2) employing the standard practice of applying a suitable voltage pulse of appropriate magnitude and duration at the workpiece tip to remove one or more hydrogen atoms, or (3) applying a proto-Hydrogen Abstraction tip or Hydrogen Abstraction Tool to the workpiece tip.

Figure 17A:
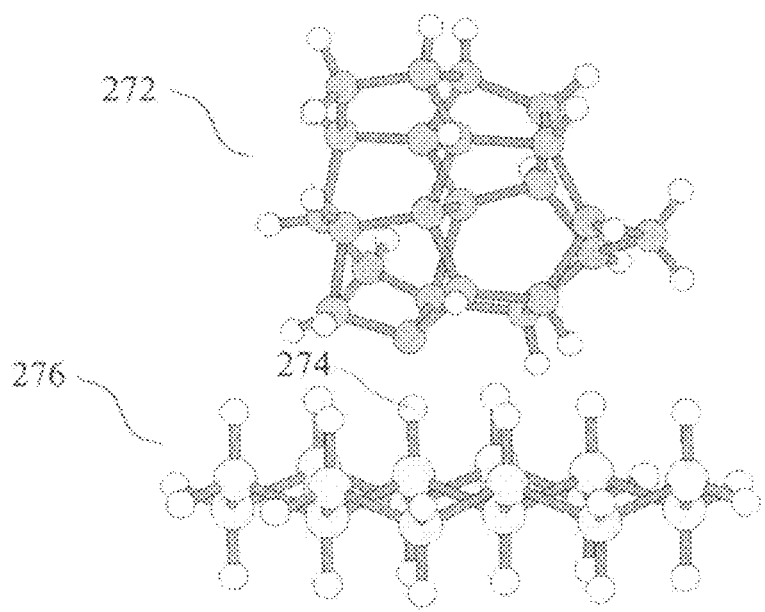
FIG. 17A shows proto-Silicon Radical tip being converted to a proto-Silicon Hydrogen Donation tip.
Figure 17B:
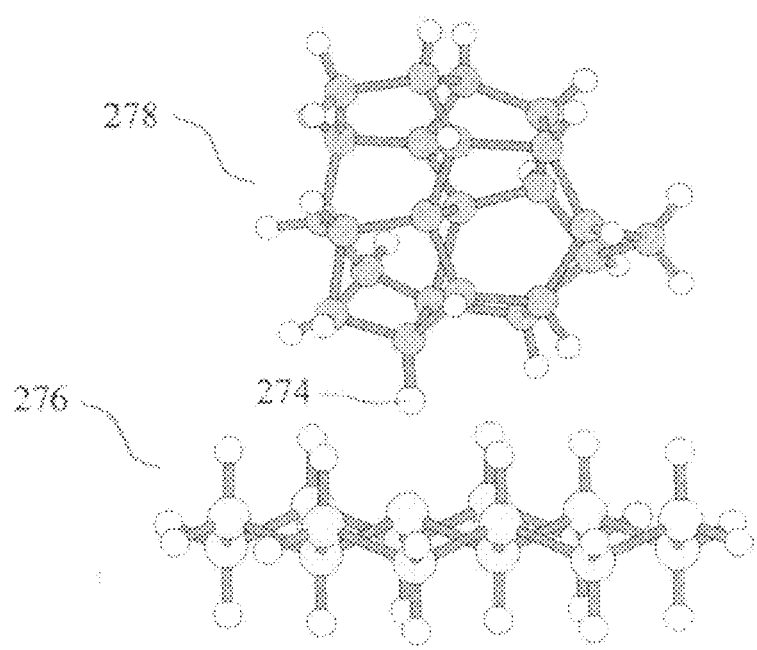
FIG. 17B shows the converted proto-Silicon Hydrogen Donation tip.

FIG. 17A illustrates the proto-Silicon Radical tip 272 being converted to the proto-Silicon Hydrogen Donation tip 278 illustrated in FIG. 17B by touching tip 272 to a hydrogen atom 274 on a suitable presentation surface 276. Of the many possible such presentation surfaces that would be suitable, an obvious choice is a hydrogenated germanium surface. This surface, upon contact by proto-Silicon Radical tip 272, transfers hydrogen atom 274 from the germanium surface 276 (where the hydrogen is more weakly bound to a germanium) to the proto-Silicon Radical tip 272 (where the hydrogen is more strongly bound to a silicon atom). The resulting proto-Silicon Hydrogen Donation tip 278 makes a suitable hydrogen donation tool.

The proto-Silicon Methylene tip. Once fabricated, the proto-Silicon Radical tip is touched to a .CH$_2$ group on a suitable presentation surface to create the functional equivalent of a GermylMethylene Tool. This functional equivalent may be called a proto-Silicon Methylene tip.

Figure 18A:
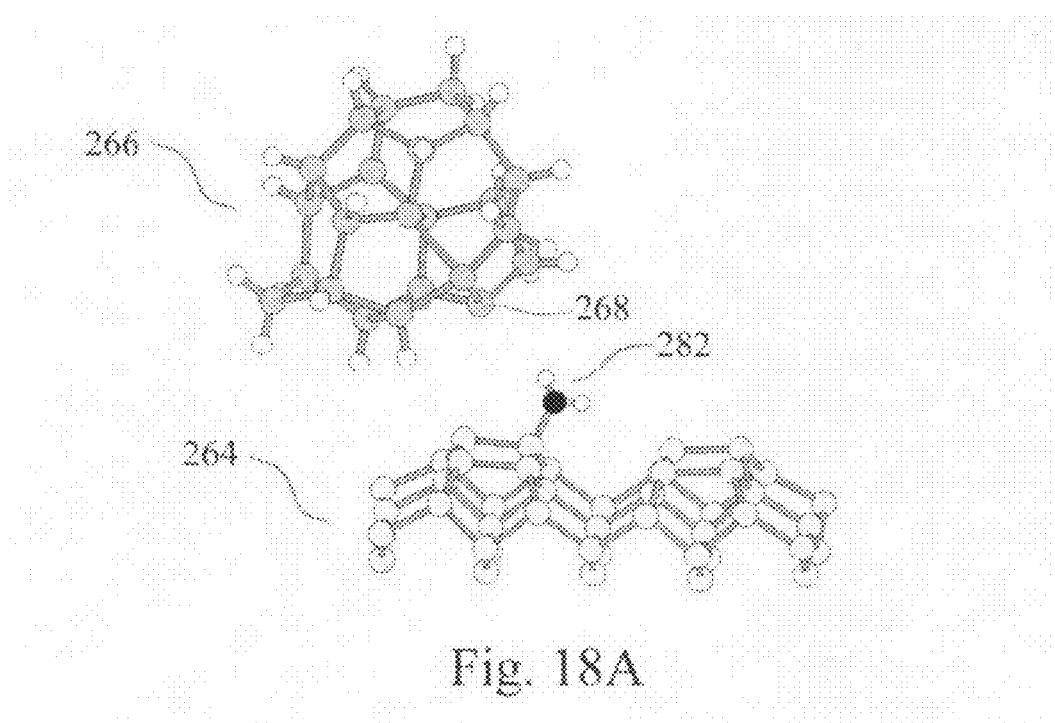
FIG. 18A shows charging a proto-Silicon Radical tip.

More generally, any radical tip, including the proto-Silicon Radical tip, can be charged by using many possible methods, as exemplified by the following series of steps illustrated by FIG. 18A:

(1) CH$_3$ groups are distributed on a suitable presentation surface 264.

(2) A proto-Hydrogen Abstraction tip removes a selected hydrogen from a specific CH$_3$ group chemisorbed to the presentation surface, leaving .CH$_2$ group 282 chemisorbed to presentation surface 264.

(3) Proto-Silicon Radical tip 266 approaches .CH$_2$ group 282 (chemisorbed to presentation surface 264).

(4) The radical site 268 on proto-Silicon Radical tip 266 bonds with .CH$_2$ group 282 on presentation surface 264.

Figure 18B:
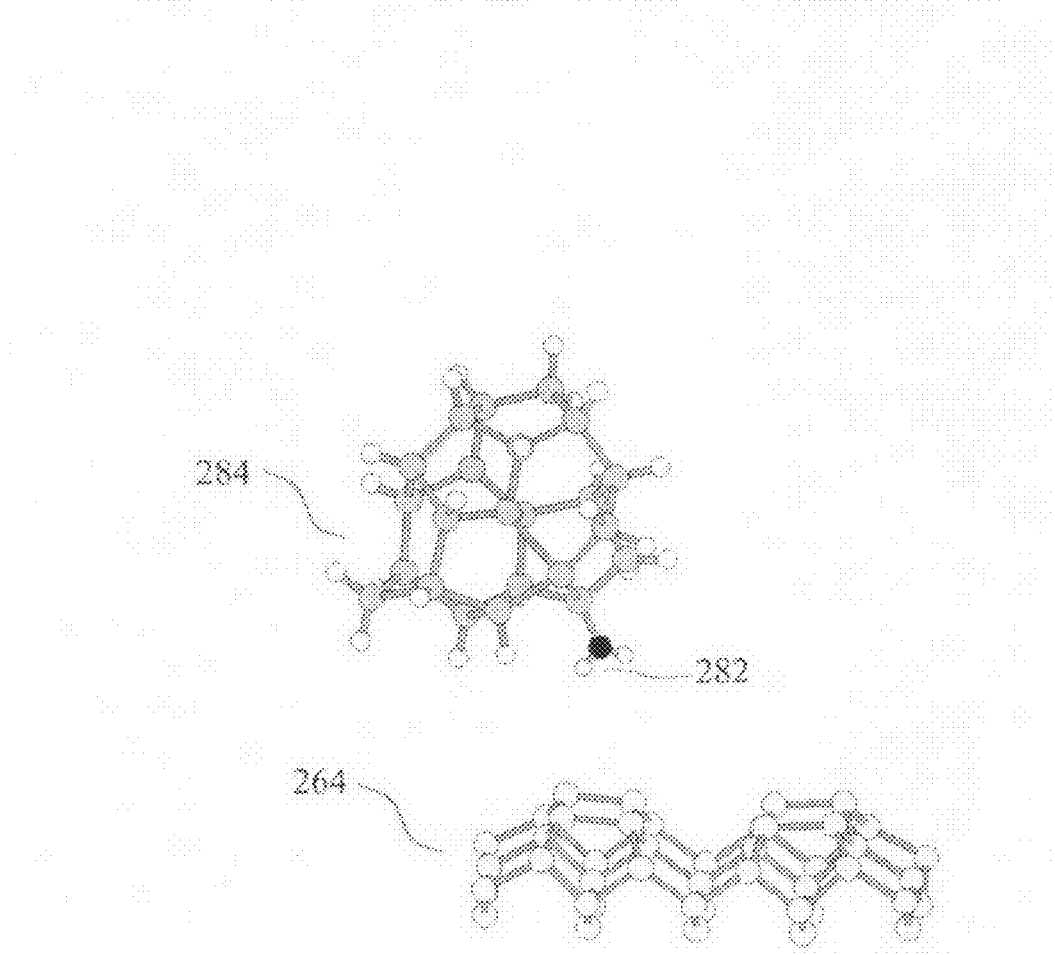
FIG. 18B shows fabrication of a proto-Silicon Methylene tip.

(5) In FIG. 18B, the proto-Silicon Methylene tip 284 is withdrawn from presentation surface 264 by the application of mechanical force, taking .CH$_2$ group 282 with it, resulting in the fabrication of proto-Silicon Methylene tip 284 from proto-Silicon Radical tip 266. Because of the relatively low reliability and the possibility of positioning errors while using these early tips, it may be necessary to test the tip after the fifth step to determine if .CH$_2$ group 282 has in fact attached to proto-Silicon Radical tip 284 upon its withdrawal.

The Adamantane Radical Tool. The fabrication of the tools of the minimal toolset using the above-described set of proto-tools can now begin.

The proto-tools including the proto-Hydrogen Abstraction tip, the proto-Silicon Hydrogen Donation tip, the proto-Silicon Radical tip, and the proto-Silicon Methylene tip can be used in subsequent reactions to make the first Adamantane Radical Tool. In these reactions the proto-Hydrogen Abstraction tip would be used in place of the Hydrogen Abstraction Tool, the proto-Silicon Radical tip would be used in place of the Germanium Radical Tool, the proto-Silicon Methylene tip would be used in place of the GermylMethylene Tool, and the proto-Silicon Hydrogen Donation tip would be used in place of the Hydrogen Donation Tool.

As the reactions are intended to provide general mechanisms for fabricating a wide range of structures involving hydrogen, carbon and germanium, some simplifications can be made because the objective during the bootstrap process is to manufacture a more limited set of structures—in particular, an initial set of molecular tools that need not provide any further functionality.

Tools generally have a tooltip and a handle. The handle can be a pyramidal structure built on a small bulk produced diamond surface. A sufficient handle need be little more than an approximately pyramidal structure having an apex suitable for mounting a tooltip.

In one preferred embodiment, a suitable handle can be fabricated by starting with a small bulk produced diamond surface. While various diamond surfaces can be used, the ring closure reactions are particularly simple when the diamond C(110) surface is used.

FIG. 19A illustrates this surface consisting of staggered rows of atomic-scale troughs. Fabrication of additional C(110) surface takes place when a zig-zag chain of carbon atoms is emplaced straddling the length of an existing trough. Two zig-zag chains added in adjacent troughs form a new trough between them, atop which an additional chain of carbon atoms can be added. Construction of a single zig-zag chain can proceed by adding single carbon atoms to the end of the chain.

Fabrication of a suitable handle using the proto-tools starting with a hydrogenated diamond C(110) surface begins as follows: (1) abstract a single hydrogen from the surface using a proto-Hydrogen Abstraction tip, creating a radical site; (2) add a .CH$_2$ group at the radical site using a proto-Silicon Methylene tip; and (3) add a hydrogen atom to the added .CH$_2$ group using a proto-Silicon Hydrogen Donation tip. FIG. 19B illustrates how this three-step reaction sequence adds a CH$_3$ group containing carbon atom 292 to the left hand side of a trough on the C(110) surface.

FIG. 19C illustrates how an additional CH$_3$ group containing carbon atom 294 is added by the same method on the right side of the trough. After two methyl groups have been added on opposite sides of the same trough, two proto-Hydrogen Abstraction tips are applied, one to each methyl group, yielding two .CH$_2$ groups in which both carbon 292 and carbon 294 are radicals, which then bond via radical coupling to form a single CH$_2$CH$_2$ group, constituting one "zig" of a zig-zag chain on the C(110) surface, as illustrated in FIG. 19D. A "zag" is then added by bonding in similar manner a third methyl group on the left hand side of the trough next to the attachment site of the first methyl group, across the trough from the attachment site of the second methyl group. A sequential application of two more proto-Hydrogen Abstraction tips to the second CH$_2$ group and the third methyl group yields two new radical sites which then bond via radical coupling, now forming a three-carbon CH$_2$CHCH$_2$ "zig-zag" sequence straddling the trough of the C(110) surface. This process is continued to produce the first zig-zag chain of desired length in the lowest (most foundational) layer of the tool handle. Following the addition of this zig-zag chain, a second, third, and following chains are added in adjacent troughs on the initial C(110) surface.

This method is used to fabricate a new layer of the C(110) surface, on top of the original surface, of some specific desired size. The process is then repeated, building up a second new layer that is slightly smaller in both lateral dimensions than the first. A third layer, similarly slightly smaller than the second layer, continues this process. Additional new layers decreasing in lateral extent are fabricated until the apex of the resulting pyramid is small enough (e.g., the width of a single adamantane cage) to provide a suitable base for the intended tool whose handle is being manufactured.

In the case of the Adamantane Radical Tool, the tooltip culminates in a single bridgehead carbon atom at the apex of the pyramid so constructed. The bridgehead carbon atom apex is either manufactured in an unhydrogenated state or is dehydrogenated after manufacture using a proto-Hydrogen Abstraction tip or Hydrogen Abstraction Tool. This sequence of reactions for building the Adamantane Radical Tool is very simple because it requires only the application of a single tool or tip at a time to build the necessary handle structure. Since the handle is built layer by layer, the aspect ratio of the initial bootstrapped tips that are used during the fabrication process can be quite poor because the workpiece is geometrically accessible and all multi-tip operations are eliminated. The aspect ratio of the manufactured tools is improved during successive toolbuilding iterations.

Other tools are constructed by a similar sequence, but with the final apex structures and modifications thereto fabricated using a slightly different sequence of reactions. For example, the Hydrogen Abstraction Tool can be directly fabricated from the Adamantane Radical Tool, as can the Germylene Tool. It is also possible to use alternative tools, tips and processes that are less reliable at higher temperatures but which, when operated at a sufficiently low temperature, become reliable enough for use during the bootstrap process—as for example a proto-Silicon Carbene tip (which is not employed in the bootstrap process described above but could be used in an alternative process to insert a third carbon atom between two previously bonded carbon atoms in a growing diamond surface).

The Hydrogen Abstraction Tool. The Hydrogen Abstraction Tool is fabricated by touching the radical at the tip of the Adamantane Radical Tool to a $C_2$ dimer on a suitable presentation surface.

The Methylene Tool. The Adamantane Radical Tool is also used to make the Methylene Tool by touching the radical tip of the Adamantane Radical Tool to a $.CH_2$ group on a suitable presentation surface, in a method analogous to that used during the bootstrap procedure to fabricate the proto-Silicon Methylene tip.

The Germylene Tool and the Proto-Silicon Germanium tip. Next, the Adamantane Radical Tool is used to make a Germylene Tool or the proto-Silicon Radical tip is used to make a proto-Silicon Germanium tip. The Germylene Tool and the proto-Silicon Germanium tip have similar functionality, so the choice about which one to use during the bootstrap sequence depends on specific issues of implementation convenience that will be evident to practitioners skilled in the art.

The Germylene Tool (or the proto-Silicon Germanium tip if fabricated) can be fabricated by touching an Adamantane Radical Tool or a proto-Silicon Radical tip (respectively) to a $GeH_2$ group on a germanium presentation surface, in a fashion similar to the proto-Silicon Methylene tip fabrication sequence illustrated in FIG. 18 but with the $.CH_2$ group 282 replaced by a $.GeH_2$ group.

The Germanium Radical Tool. Either the Germylene Tool or the proto-Silicon Germanium tip can then be used during fabrication of the first Germanium Radical Tool. As the Si—Ge bond is weaker than the C—Ge bond, the reaction sequence used with the proto-Silicon Germanium tip is simpler than the reaction sequence used with the Methylene Tool.

Alternatively, the Germanium Radical Tool can be fabricated by a sequence of reactions similar to those described for the Adamantane Radical Tool and illustrated in FIG. 19, with but one exception. The single use of the proto-Silicon Methylene tip that adds the carbon atom destined to be the radical carbon at the tip of the Adamantane Radical Tool is replaced by a single use of either (1) the Germylene Tool or (2) the proto-Silicon Germanium tip, as is convenient. The remaining reactions in the sequence continue as before. As the single use of the Germylene Tool or the proto-Silicon Germanium tip is the only use of either one of these items in the entire reaction sequence required for the fabrication of the Germanium Radical Tool, the reaction reliability for this single tool application need not be high.

The GermylMethylene and Hydrogen Donation Tools. Once fabricated, the Germanium Radical Tool can be charged by touching it to a $.CH_2$ on a suitable presentation surface, analogous to the previously described methods, producing the first GermylMethylene Tool.

The Germanium Radical Tool can also be used to make the Hydrogen Donation Tool by using the Hydrogen Abstraction recharge reaction illustrated in FIG. 12. The Hydrogen Abstraction Tool must first be used to abstract a hydrogen atom, creating a spent Hydrogen Abstraction Tool 110 requiring recharge. Then the Germanium Radical Tool 130 will bond to the spent Hydrogen Abstraction Tool 110 at the distal carbon atom 102. A second Germanium Radical Tool 224 then abstracts hydrogen 112 from the tip of the spent Hydrogen Abstraction Tool 110 to produce a new Hydrogen Donation Tool 120. The bonded Hydrogen Abstraction Tool 100 and the first Germanium Radical Tool 130 are then separated, regenerating both.

The Hydrogen Transfer and Dimer Placement Tools. As illustrated in FIG. 15, the Hydrogen Transfer Tool is fabricated by bonding a Germanium Radical Tool 130 to a spent Hydrogen Abstraction Tool 110. The Dimer Placement Tool can be made using the previous tools. The entire nine-tool minimal toolset has now been fabricated.

Summary of Bootstrap Process. The particular sequence of bootstrap operations described here is: (1) Proto-Hydrogen Abstraction tip, (2) Proto-Silicon Hydrogen Donation tip, (3) Proto-Silicon Radical tip, (4) Proto-Silicon Methylene tip, (5) Adamantane Radical Tool, (6) Hydrogen Abstraction Tool, (7) Methylene Tool, (8) Germylene Tool, (9) Proto-Silicon Germanium tip (optional), (10) Germanium Radical Tool, (11) GermylMethylene Tool, (12) Hydrogen Donation Tool, (13) Hydrogen Transfer Tool, and (14) Dimer Placement Tool. Other sequences will be apparent to practitioners skilled in the art and having the benefit of the teachings presented herein.

Bootstrapping a set of mechanosynthetic tools in an inert environment requires careful consideration of the reactions involved. It can be simplified by the use of additional reactions, elements, conditions, or mechanisms that are used primarily or only during the bootstrap sequence. For example, if reactions are carried out at low temperature, then reliability problems which are exacerbated by thermal noise and thermally induced errors can be greatly reduced. Low temperature operation also allows the use of alternative reactions that might have unacceptably low reliability at higher temperatures. Substantially more numerous mechanosynthetic reactions are reliable at lower temperatures. Auxiliary tips and processes can be introduced to simplify the steps in the bootstrap sequence, much as scaffolding can be used during the construction of a building. The mechanisms for providing feedstock molecules and for disposing of excess atoms can also be chosen to simplify the bootstrap process.

Although critical in the early stages of the development of mechanosynthesis, the bootstrap process is likely to become almost immediately obsolete. Once the bootstrap proto-tools have fabricated any reasonably complete set of atomically precise mechanosynthetic tools, then this complete set of more sophisticated tools can be employed exclusively thereafter, with the original bootstrap proto-tools having no further use.

What is claimed is:

1. A tooltip for performing a site-specific mechanosynthetic chemical reaction wherein a reactant or plurality of reactants are selected from the group consisting of the carbon group and non-metal elements, excluding the noble gases, the tooltip comprising:

a first atom or plurality of atoms arranged in an engineered atomically precise molecular structure in which either or both the bonding pattern and the electronic state of said first atom or plurality of atoms is altered during said site-specific mechanosynthetic chemical reaction; and a second atom or plurality of atoms affixed to said first atom or plurality of atoms, said second atom or plurality of atoms arranged in an engineered atomically precise molecular structure in which neither the bonding pattern nor the electronic state of said second atom or plurality of atoms is altered during said site-specific mechanosynthetic chemical reaction;

wherein there is a barrier to undesired reactions sufficient to achieve a desired reliability of operation at a given temperature because the application of mechanical force is required to drive a desired chemical reaction.

2. The mechanosynthetically active tooltip of claim 1 wherein the elements for performing reactions are selected from the group consisting of C (carbon), N (nitrogen), O (oxygen), H (hydrogen), F (fluorine), Si (silicon), Ge (germanium), Sn (tin), and Pb (lead).

3. The mechanosynthetically active tooltip of claim 1 wherein a reversible bonding tool bonds to a workpiece and permits kinematic manipulation of the workpiece without altering the atomic constituency of the workpiece.

4. A tooltip for performing a site-specific mechanosynthetic chemical reaction wherein a reactant or plurality of reactants are selected from the group consisting of the carbon group and non-metal elements, excluding the noble gases, the tooltip comprising:

a first atom or plurality of atoms arranged in an engineered atomically precise molecular structure in which either or both the bonding pattern and the electronic state of said first atom or plurality of atoms is altered during said site-specific mechanosynthetic chemical reaction; and a second plurality of atoms affixed to said first atom or plurality of atoms, said second plurality of atoms arranged in an engineered atomically precise molecular structure in which neither the bonding pattern nor electronic state is altered during said site- specific mechanosynthetic chemical reaction, said engineered atomically precise molecular structure comprising a polycyclic closed shell molecular structure composed of atoms selected from the group consisting of C (carbon), N (nitrogen), O (oxygen), H (hydrogen), F (fluorine), Si (silicon), Ge (germanium), Sn (tin), and Pb (lead), wherein at least one structural substituent atom is bonded to three other structural atoms and is terminated by either one or more nonstructural atoms, or a structural atom that is bonded to two other structural atoms and is terminated by one or more nonstructural atoms;

wherein there is a barrier to undesired reactions sufficient to achieve a desired reliability of operation at a given temperature because the application of mechanical force is required to drive a desired chemical reaction.

5. The tooltip of claim 4 wherein said at least one structural substituent atom is selected from the group consisting of C (carbon), Si (silicon), and Ge (germanium), wherein said structural substituent atom is bonded to three other structural atoms; or is a N (nitrogen) atom, wherein said atom is bonded to two other structural atoms.

6. The tooltip of claim 4 wherein said at least one structural substituent atom is either partly terminated, or completely terminated, by a single transfer substituent atom selected from the group consisting of .C: (carbon triradical), F (fluorine), .Ge: (germanium triradical), H (hydrogen), N: (nitrogen diradical), O. (oxygen monoradical), and .Si: (silicon triradical).

7. The tooltip of claim 4 wherein said at least one structural substituent atom is either partly terminated, or completely terminated, by a single transfer substituent atom bonded to a single transfer passivating atom, wherein said transfer substituent atom is selected from the group consisting of C (carbon), Ge (germanium), N (nitrogen), O (oxygen), and Si (silicon), and said transfer passivating atom is selected from the group consisting of F (fluorine) and H (hydrogen).

8. The tooltip of claim 4 wherein said at least one structural substituent atom is either partly terminated, or completely terminated, by a single transfer substituent atom bonded to one or two transfer passivating atoms, wherein said single transfer substituent atom is selected from the group consisting of C (carbon), Ge (germanium), F (fluorine), H(hydrogen), N (nitrogen), and Si (silicon), and in the case where said single transfer substituent atom is bonded to two transfer passivating atoms, said two transfer passivating atoms are selected from the group consisting of F (fluorine) and H (hydrogen).

9. The tooltip of claim 4 wherein said at least one structural substituent atom is either partly terminated, or completely terminated, by a single transfer substituent atom bonded to one, two, or three transfer passivating atoms, wherein said single transfer substituent atom is selected from the group consisting of C (carbon), Ge (germanium), H (hydrogen), N (nitrogen), O (oxygen) and Si (silicon), and in the case where said single transfer substituent atom is bonded to two or three transfer passivating atoms, said two or three transfer passivating atoms are selected from the group consisting of F (fluorine) and H (hydrogen).

10. The tooltip of claim 4 wherein said structural substituent atom is bonded to the proximal carbon atom of a triple-bonded C≡C moiety, and the distal carbon atom of the triple-bonded C≡C moiety is terminated by a single transfer substituent atom selected from the group consisting of F (fluorine), H (hydrogen), N (nitrogen), and O (oxygen).

11. A tool for performing a site-specific mechanosynthetic chemical reaction wherein a reactant or plurality of reactants are selected from the group consisting of the carbon group and non-metal elements, excluding the noble gases, the apparatus tool comprising:

a first atom or plurality of atoms of arranged in an engineered atomically precise molecular structure in which either or both the bonding pattern and the electronic state of said first atom or plurality of atoms is altered during said site-specific mechanosynthetic chemical reaction; and a second plurality of atoms consisting of an engineered atomically precise molecular structure in which neither bonding pattern nor electronic state is altered during said site-specific mechanosynthetic chemical reaction, said engineered atomically precise molecular structure comprising a polycyclic closed shell molecular structure composed of atoms selected from the group consisting of C (carbon), N (nitrogen), O (oxygen), H (hydrogen), F (fluorine), Si (silicon), Ge (germanium), Sn (tin), and Pb (lead), wherein a structural substituent atom is bonded to three other structural atoms and is terminated by either one or more nonstructural atoms, or a structural atom that is bonded to two other structural atoms and is terminated by one or more nonstructural atoms; and a handle structure comprising a third plurality of atoms in which said handle structure is bonded to said second plurality of atoms whereby said handle structure can be manipulated by a system capable of atomically precise positional control; wherein there is a barrier to undesired reactions sufficient to achieve a desired reliability of operation at a given temperature because the application of mechanical force is required to drive a desired chemical reaction.

12. The tool of claim 11 wherein said handle structure is selected from a group consisting of: a crystallographically-matched adamantane cage; a principal cubic or hexagonal diamond C(111), C(110), or C(100) surface; a vicinal diamond surface; and an adamantane-like molecular structure.

13. The tool of claim 11 wherein said tool can be bonded to a workpiece and permits kinematic manipulation of said workpiece, and debonded from said workpiece without altering the atomic constituency of said workpiece.

14. The tool of claim 11 wherein the handle structure conjoins a plurality of mechanosynthetically active tooltips such that said plurality of mechanosynthetically active tooltips can be operated as a single mechanosynthetically active tool.

15. A mechanosynthetic apparatus capable of performing a site-specific mechanosynthetic chemical reaction using reactants selected from the group consisting of the carbon group and non-metals, excluding noble gases, wherein there is a barrier to undesired reactions sufficient to achieve a desired reliability of operation at a given temperature because the application of mechanical force is required to drive a desired chemical reaction, comprising:

a mechanosynthetically active tooltip; and
a means for supplying reactants to said mechanosynthetically active tooltip;
a means for keeping said mechanosynthetically active tooltip under positional control;
a means for keeping a workpiece under positional control with respect to said mechanosynthetically active tooltip;
a means for keeping said mechanosynthetically active tooltip and said workpiece in an inert environment;
and a means for regulating the temperature of said mechanosynthetically active tooltip and said workpiece.

16. The apparatus of claim 15 where the elements for performing said site-specific mechanosynthetic chemical reaction are selected from the group consisting of C (carbon), N (nitrogen), O (oxygen), H (hydrogen), F (fluorine), Si (silicon), Ge (germanium), Sn (tin), and Pb (lead).

17. The apparatus of claim 15 wherein said site-specific mechanosynthetic chemical reaction forms a new chemical bond between one or more atoms on said workpiece and one or more atoms on said mechanosynthetically active tooltip.

18. The apparatus of claim 15 wherein said site-specific mechanosynthetic chemical reaction causes a transfer of one or more atoms between the workpiece and the mechanosynthetically active tooltip.

19. The apparatus of claim 15 where said site-specific mechanosynthetic chemical reaction results in a change to the molecular geometry or electronic state of a workpiece.

20. The apparatus of claim 15 wherein the temperature is maintained at or below 77°K.

21. The apparatus of claim 15 wherein the temperature is maintained at or below 4°K.

22. The apparatus of claim 15 wherein said inert environment is a vacuum.

23. The apparatus of claim 15 wherein said at least one structural substituent atom is selected from the group consisting of C (carbon), Si (silicon), and Ge (germanium), wherein such atom is bonded to three other structural atoms; or is a N (nitrogen) atom, bonded to two other structural atoms.

24. The apparatus of claim 15 wherein said at least one structural substituent atom is left unterminated.

25. The apparatus of claim 15 wherein said at least one structural substituent atom is either partly terminated, or completely terminated, by a single transfer substituent atom selected from the group consisting of: .C: (carbon triradical), F (fluorine), .Ge: (germanium triradical), H (hydrogen), N: (nitrogen diradical), O. (oxygen monoradical), and .Si: (silicon triradical).

26. The apparatus of claim 15 wherein said at least one structural substituent atom is either partly terminated, or completely terminated, by a single transfer substituent atom bonded to a single transfer passivating atom, wherein the transfer substituent atom is selected from the group consisting of .C: (carbon triradical), F (fluorine), .Ge: (germanium triradical), H (hydrogen), N: (nitrogen diradical), O. (oxygen monoradical), and .Si: (silicon triradical), and said transfer passivating atom is selected from the group consisting of F (fluorine) and H (hydrogen).

27. The apparatus of claim 15 wherein said at least one structural substituent atom is either partly terminated, or completely terminated, by a single transfer substituent atom bonded to one or two transfer passivating atoms, wherein said single transfer substituent atom is selected from the group consisting of: .C: (carbon triradical), F (fluorine), .Ge: (germanium triradical), H (hydrogen), N: (nitrogen diradical), O. (oxygen monoradical), and .Si: (silicon triradical), or said two transfer passivating atoms are selected from the group consisting of F (fluorine) and H (hydrogen).

28. The apparatus of claim 15 wherein said at least one structural substituent atom is either partly terminated, or completely terminated, by a single transfer substituent atom bonded to one, two, or three transfer passivating atoms, wherein said single transfer substituent atom is selected from the group consisting of .C: (carbon triradical), F (fluorine), .Ge: (germanium triradical), H (hydrogen), N: (nitrogen diradical), O. (oxygen monoradical), and .Si: (silicon triradical); or said two or said three passivating atoms are selected from the group consisting of F (fluorine) or H (hydrogen).

29. The apparatus of claim 15 wherein said structural substituent atom is bonded to the proximal carbon atom of a triple-bonded C≡C moiety, and the distal carbon atom of the triple-bonded C≡C moiety is terminated by a single transfer substituent atom selected from the group consisting of F (fluorine), H (hydrogen), N (nitrogen), and O (oxygen).

30. The apparatus of claim 15 wherein a plurality of such apparatuses are operated in parallel to perform a plurality of mechanosynthetic reactions.

31. The apparatus of claim 15 wherein a plurality of said apparatuses are operated in cooperation to perform a single mechanosynthetic reaction.

32. The apparatus of claim 15 whereby said active tip of the mechanosynthetically active tooltip or the mechanosynthetically active tool follows a positionally controlled trajectory with respect to a workpiece, and thus causes a mechanosynthetic chemical reaction to occur at a specific site on the workpiece.

33. The apparatus of claim 15 wherein said mechanosynthetically active tooltip is bonded to a workpiece, and the further positionally controlled movement of the bonded tooltip causes a change in the molecular geometry or the electronic state of one or more atoms comprising the workpiece.

34. The apparatus of claim 15 wherein said active tip of said mechanosynthetically active tooltip or said mechanosynthetically active tool follows a positionally controlled trajectory with respect to a workpiece, causing a mechanosynthetic chemical reaction to occur at a specific site on the workpiece.

35. The apparatus of claim 15 wherein said mechanosynthetically active tooltip is bonded to said workpiece, and the further positionally controlled movement of said bonded tooltip causes a change in the molecular geometry or the electronic state of one or more atoms comprising said workpiece.

* * * * *